(12) United States Patent
Carvalho Sousa et al.

(10) Patent No.: US 10,209,178 B2
(45) Date of Patent: Feb. 19, 2019

(54) OPTICAL SYSTEM FOR PARAMETER CHARACTERIZATION OF AN ELEMENT OF BODY FLUID OR TISSUE

(71) Applicants: UNIVERSIDADE DO MINHO, Braga (PT); Nuno Jorge Carvalho Sousa, Porto (PT); Rui Miguel Da Costa Martins, Maia (PT)

(72) Inventors: Nuno Jorge Carvalho Sousa, Porto (PT); Rui Miguel Da Costa Martins, Maia (PT); Ricardo Alberto Alvarez Osorio, Porto (PT)

(73) Assignees: UNIVERSIDADE DO MINHO, Barga (PT); Nuno Jorge Sousa, Porto (PT); Rui Miguel Da Costa Martins, Maia (PT)

( * ) Notice: Subject to any disclaimer, the term of this patent is extended or adjusted under 35 U.S.C. 154(b) by 75 days.

(21) Appl. No.: 14/765,242

(22) PCT Filed: Jan. 31, 2014

(86) PCT No.: PCT/IB2014/058709
§ 371 (c)(1),
(2) Date: Jul. 31, 2015

(87) PCT Pub. No.: WO2014/118745
PCT Pub. Date: Aug. 7, 2014

(65) Prior Publication Data
US 2015/0369725 A1 Dec. 24, 2015

Related U.S. Application Data

(63) Continuation-in-part of application No. PCT/IB2013/056229, filed on Jul. 29, 2013.

(30) Foreign Application Priority Data

Jan. 31, 2013 (PT) .......................... 106759

(51) Int. Cl.
*G01N 21/25* (2006.01)
*A61B 5/00* (2006.01)
(Continued)

(52) U.S. Cl.
CPC ......... *G01N 21/255* (2013.01); *A61B 5/0075* (2013.01); *A61B 5/1455* (2013.01);
(Continued)

(58) Field of Classification Search
CPC .. G01N 21/255; A61B 5/1455; A61B 5/1495; A61B 5/14546; A61B 5/7246; A61B 5/6824; A61B 5/14532; A61B 5/0075
See application file for complete search history.

(56) References Cited

U.S. PATENT DOCUMENTS 566,956 A 9/1896 Wright
4,866,644 A 9/1989 Shenk
(Continued)

FOREIGN PATENT DOCUMENTS

GB 2489717 10/2012
WO WO 99/18847 4/1999
(Continued)

OTHER PUBLICATIONS

Jaffe M. "Ueber den Niederschlag, welchen Pikrinsaure in normalem Harn erzeugt und uber eine neue Reaction des Kreatinins." Hoppe Seylers Z Physiol Chem Jan. 1886;10:391-400.
(Continued)

*Primary Examiner* — Dominic J Bologna
(74) *Attorney, Agent, or Firm* — Leason Ellis LLP

(57) ABSTRACT

Biophotonic device for the point-of-care, real-time, non-invasive determination of parameters with diagnostic relevance, in particular an optical system for parameter characterization of an element of body fluid or tissue comprising an optical device which comprises: a light source for emit-
(Continued)

ting light onto the element; and a spectrometer for recording the spectrum of light from the element, said light from the element being of transmittance, reflectance or Raman scattering of the emitted light by said element; the optical system further comprising a data processing module configured to: convert the recorded spectrum by a conversion matrix into a standardized spectrum, wherein said conversion matrix has been obtained by calibrating the optical system spectrum response against a spectrum reference; pre-process the converted spectrum; correlate, for parameter quantification, the converted pre-processed spectrum with pre-obtained spectral bands for each parameter; said spectrum being contained within uv-vis-nir wavelengths. Also methods of operating said system.

20 Claims, 12 Drawing Sheets

(51) Int. Cl.
G01N 21/65 (2006.01)
A61B 5/145 (2006.01)
G01N 33/483 (2006.01)
A61B 5/1455 (2006.01)
A61B 5/1495 (2006.01)

(52) U.S. Cl.
CPC ........ A61B 5/1495 (2013.01); A61B 5/14532 (2013.01); A61B 5/14546 (2013.01); A61B 5/6824 (2013.01); A61B 5/7246 (2013.01); G01N 21/65 (2013.01); G01N 33/4833 (2013.01); A61B 2503/40 (2013.01); A61B 2560/0223 (2013.01); A61B 2560/0285 (2013.01); A61B 2560/045 (2013.01); A61B 2562/0238 (2013.01); G01N 2201/062 (2013.01); G01N 2201/0612 (2013.01); G01N 2201/12 (2013.01)

(56) References Cited

U.S. PATENT DOCUMENTS

| | | | |
|---|---|---|---|
| 4,890,619 A | 1/1990 | Hatschek | |
| 5,713,364 A * | 2/1998 | DeBaryshe | A61B 1/00059 250/461.2 |
| 5,850,623 A * | 12/1998 | Carman, Jr. | G01J 3/28 702/28 |
| 6,064,897 A | 5/2000 | Lindberg et al. | |
| 6,081,740 A * | 6/2000 | Gombrich | A61B 5/0071 600/117 |
| 6,167,290 A | 12/2000 | Yang et al. | |
| 6,246,898 B1 * | 6/2001 | Vesely | A61B 5/0422 600/424 |
| 6,587,702 B1 * | 7/2003 | Ruchti | A61B 5/0059 600/306 |
| 7,330,746 B2 | 2/2008 | Demuth et al. | |
| 7,524,671 B2 | 4/2009 | Clarke et al. | |
| 7,688,440 B2 | 3/2010 | Clarke et al. | |
| 8,013,991 B2 | 9/2011 | Maier et al. | |
| 2004/0024298 A1 | 2/2004 | Marshik-Geurts et al. | |
| 2005/0273011 A1 * | 12/2005 | Hattery | A61B 5/0059 600/476 |
| 2006/0166302 A1 | 7/2006 | Clarke et al. | |
| 2007/0224683 A1 | 9/2007 | Clarke et al. | |
| 2008/0183388 A1 * | 7/2008 | Goodrich | A61B 5/14546 701/300 |
| 2008/0221457 A1 * | 9/2008 | Zeng | A61B 5/0071 600/477 |
| 2009/0035218 A1 * | 2/2009 | Ross | A61B 5/415 424/9.1 |
| 2009/0252406 A1 | 10/2009 | Chiba | |
| 2012/0035442 A1 | 2/2012 | Barman et al. | |
| 2013/0256534 A1 * | 10/2013 | Micheels | G01N 21/255 250/339.07 |

FOREIGN PATENT DOCUMENTS

WO  WO 01/52725  7/2001
WO  WO 2004/096082  11/2004

OTHER PUBLICATIONS

Richmond W. "Preparation and properties of a cholesterol oxidase from *Nocardia* sp. and its application to the enzymatic assay of total cholesterol in serum." Clin Chem Dec. 1973;19(12)1 350-6.

Allain CC, Poon LS, Chan CS, et al. "Enzymatic determination of total serum cholesterol." Clin Chem Apr. 1974;20(4):470-5.

Fossati P, Prencipe L. "Serum triglycerides determined colorimetrically with an enzyme that produces hydrogen peroxide." Clin Chem Oct. 1982;28:2077-80.

McGowan MW, Artiss JD, Strandbergh DR, et al. "A peroxidase-coupled method for colorimetric determination of serum triglycerides." Clin Chem Mar. 1983;29:538-42.

Trivedi R, Rebar L, Berta E, et al. "New enzymatic method for serum uric acid at 500 nm." Clin Chem Nov. 1978; 24(11)1908-11.

Kabasakalian P, Kalliney S, Wescott A. "Determination of uric acid in serum, with use of uricase and tribromophenol-aminoantipyrine chromogen." Clin Chem Feb. 12, 1973;19:522.

Tietz NW, Burtis CA, Duncan P, et al. "A reference method for measurement of alkaline phosphatase activity in human serum." Clin Chem May 1983;29(5):751-6.

Burns DA, Ciurczak EW. Jun. 28, 2001. "Handbook of near-infrared analysis." 2nd Ed. Marcell Dekker, Inc.

Feudale RN, Woody NA, Tan H, Myles AJ, Brown SD, Ferré J. Nov. 28, 2002."Transfer of multivariate calibration models: a review." Chemo. Intl. Lab. Sys. 64: 181-203.

Woody NA, Feudale RN, Myles AJ, Brown SD. Apr. 7, 2004. "Transfer of multivariate calibration between four near infrared spectrometers using orthogonal signal correction." Anal Chem. May 1, 2004; 76(9):2595-600.

Wangdong Ni, Steven D Brown, Ruilin Man. Feb. 1, 2011. "Stacked PLS for calibration transfer without standards." J. Chemometrics, 25: 130-137.

Forina M. et al. Feb. 1995. "Transfer of calibration function in near infrared spectroscopy." Chem. and Int. Lab. Sys. 27(2): 189-203.

Fan W, Liang Y, Yuan D, Wang J. Aug. 8, 2008. "Calibration model transfer for near-infrared spectra based on canonical correlation analysis." Analytica Chimica Acta, 623(1): 22-29.

Andrews DT, Warzel PP. Sep. 19, 1997. "Application of maximum likelihood principal component analysis: incomplete datasets and calibration transfer."Analytical Chemica Acta, 350: 341-352.

Xie Y, Hopke PK Mar. 29, 1999. "Calibration transfer as a data reconstruction problem" Analytical Chemica Acta, 384: 193-205.

Despagne F, Massart DL, Jansen M, Daalen H. Feb. 21, 2000. "Intersite transfer of industrial calibration models." Analytical Chemica Acta, 384: 193-205.

Ni W, Brown SD, Man R. Feb. 28, 2010. "Data fusion in multivariate calibration transfer." Analytical Chemica Acta, 661: 133-142.

Shenk JS, Westerhaus MO. 1996. "New standardization and calibration procedures for NIRS analytical systems." Crop Science, 31:1694-1696. Published Nov. 1991.

Wang Y, Kowalski BR. Apr. 1992. "Calibration transfer and measurement stability of NIR spectrometers." Applied Spectroscopy, 46: 764-771.

Wang Y, Veltkamp DJ, Kowalski BR. Dec. 1991 "Multivariate instrument standardization." Anal. Chem. 63(23): 2750-2756.

Barring HK, Boelens HFM, Noord OE, Smilde, AK. Apr. 2001. "Optimizing meta-parameters in continuous piecewise direct standardization." Applied Spectroscopy, 55(4):458-466.

Geladi P, Barring H, Dabakk E, Trygg J, Antti H, Wold S, Karlberg B. Oct. 11, 1999. "Calibration transfer for predicting lake-water pH

(56) References Cited

OTHER PUBLICATIONS from near infrared spectra of lake sediments." Journal of Near Infrared Spectroscopy, 7:251-264.

Walzack B, Massart DL. Aug. 1997. "Wavelet packet transform applied to a set of signals: a new approach to the best basis selection." Chem. Intel. Lab Sys. 78: 39-50.

Walzack B, Bouveresse E, Massart DL. Feb. 1997. "Standardization of near infrared spectra in the wavelet domain." Chem. Intel. Lab Sys. 36: 41-51.

Lerner JM. 2006. "Imaging spectrometer fundamentals for resarchers in the biosciences—a tutorial." Cytometry Part A 69A: 712-734. Accepted Dec. 20, 2005.

Kauppinen J., Partanen J. 2001. "Fourier transforms in spectroscopy." Wiley-VCH, Berlin. Published online May 16, 2002.

Talke, H, Schubert; GE 1965, "Enzyme determination of urea in blood serum by the Warburg optical test," Klinische Wochenschrift, 43 174-175, Oct. 2, 1964.

* cited by examiner

OPTICAL SYSTEM FOR PARAMETER CHARACTERIZATION OF AN ELEMENT OF BODY FLUID OR TISSUE

CROSS REFERENCE TO RELATED APPLICATIONS

The present application is a U.S. National Phase of International Patent Application PCT/IB2014/058709, filed Jan. 31, 2014, which claims priority to Portuguese Application No. 106759, filed on Jan. 31, 2013, and is a continuation-in-part of PCT/IB2013/056229, filed on Jul. 29, 2013, which are incorporated by reference as if expressly set forth in their respective entireties herein.

TECHNICAL FIELD

The present disclosure relates the field of biophotonic equipments applied to healthcare; in particular, it relates to a biophotonic device for the point-of-care, real-time, non-invasive determination of parameters with diagnostic relevance, of tissue (e.g. blood, adipose tissue) samples or in-vivo (e.g. by skin contact).

BACKGROUND ART

Current biophotonic systems present a series of technical limitations that do not allow them to be used as a real-time holistic health system at the point-of-care.

It is one a goal of the present disclosure to provide such system.

SUMMARY

It is disclosed an optical system for parameter characterization of an element of body fluid or tissue comprising an optical device which comprises:
 a light source for emitting light onto the element; and
 a spectrometer for recording the spectrum of light from the element, said light from the element being of transmittance, reflectance or Raman scattering of the emitted light by said element;
the optical system further comprising a data processing module configured to:
 convert the recorded spectrum by a conversion matrix into a standardized spectrum, wherein said conversion matrix has been obtained by calibrating the optical system spectrum response against a spectrum reference;
 pre-process the converted spectrum;
 correlate, for parameter quantification, the converted pre-processed spectrum with pre-obtained spectral bands for each parameter;
said spectrum being contained within uv-vis-nir wavelengths, in particular 200-2500 nm wavelengths, further in particular 200-1200 nm wavelengths.

In particular, the calibration was carried out against a spectrum reference previously measured by a reference spectrometer.

In particular, the pre-obtained spectral bands for each parameter were previously measured by the reference spectrometer.

In particular, the reference spectrometer has improved or equal optical resolution, noise rejection, or light sensitivity in comparison with the optical device spectrometer.

In an embodiment, the spectral bands for each parameter were pre-obtained by:
 obtaining sample spectra with known parameter values;
 pre-processing the obtained sample spectra;
 correlating the pre-processed spectra with the known parameter values in order to obtain the spectral bands for each parameter.

In an embodiment, the spectral bands for each parameter were pre-obtained, explicitly or implicitly, by correlation through multivariate regression, latent variable model, PLS, two-step PLS, S-PLS, canonical correlation, or artificial neural network, or support vector machines.

In an embodiment, the spectrum calibrating for obtaining said conversion matrix comprises computing the warping of a conversion matrix function to matching both frequency and intensity of the spectra of the optical device spectrum response against the frequency and intensity of a spectrum reference in particular previously measured by the reference spectrometer.

In an embodiment, the spectrum calibrating for obtaining said conversion matrix comprises:
 recording a spectrum of a previously recorded spectrum reference;
 pre-processing the recorded spectrum;
 computing the warping of said conversion matrix function such that the pre-processed recorded spectrum converted by said matrix matches the frequency and intensity of the previously recorded spectrum reference.

In particular, the recording a spectrum above comprises recording a spectrum of a spectrum reference of the same light emitting, reflecting, absorbing or scattering material of the previously recorded spectrum reference by the reference spectrometer.

In an embodiment, the pre-processing of a spectrum comprises correcting the spectrum for scattering, in particular Mie and Rayleigh scattering, and correcting for baseline-stray light.

In an embodiment, the obtained spectra, prior to spectrum pre-processing, were subjected to a super-resolution process to obtain higher spectral full width at half maximum, FWHM, than that of the optical limit of the spectrometer, said process comprising:
 calculating an interpolation model of the higher pixel resolution by local regression, and interpolating the obtained multiple spectral measurements;
 performing deconvolution of the interpolated spectral measurements to resolve convolved information below optical resolution, in particular by the apodization function of the optical device.

In an embodiment, the data processing module is configured such that spectrum recording comprises the previous steps of:
 verifying if the temperature of the light source is within predetermined limits for suitable spectrum emission;
 verifying if the temperature of the spectrometer is within predetermined limits for suitable spectrum reception; and
 if a light source reference is being used, verifying if the spectrum of the light source reference is within predetermined limits of the light source reference;
wherein data processing module will only proceed beyond the spectrum recording if the above verifications are met.

In an embodiment, the data processing module is configured to operate the spectrometer when recording a spectrum in piecewise measurement in a plurality of overlapping intervals covering the wavelength range to be recorded of the spectrometer, each interval optimized for both integration time and light intensity.

In an embodiment, the data processing module is configured such that the spectrum recording comprises interpolation of the received spectra to a higher resolution than the original spectra, in particular interpolation to at least 3 times higher resolution.

In an embodiment, the data processing module is configured such that spectrum recording comprises recording multiple spectral measurements of the same element and/or spectrum reference.

In an embodiment, the data processing module is configured such that spectrum recording comprises the previous steps of:
- recording a sample spectrum without the element to be characterized; and
- linearly calibrating the spectrometer for each frequency such that the sample spectrum matches a previously obtained reference spectrum.

In an embodiment, the element to be characterized is a body in-vivo element, in particular the optical system is arranged for parameter characterization of the body element by skin contact of the optical device, in particular by skin contact to a blood vessel or to adipose tissue body element.

In an embodiment, the element to be characterized is a sample of body fluid, in particular blood, blood serum, saliva, sweat, urine or tears, or a sample of body tissue, in particular adipose tissue.

An aspect of the disclosure is a chamber for receiving a sample of body fluid or tissue to be characterized by an optical system comprising a light source for emitting light onto the element; and a spectrometer for recording the spectrum of light from the element, said light from the element being of transmittance, reflectance or Raman scattering of the emitted light by said element.

In an embodiment, the chamber is attachable to the optical device for characterization of the element.

In an embodiment, the chamber is attachable by magnets or by mechanical pressure or mechanical fasteners.

In an embodiment, the chamber is liquid-tight.

In an embodiment, the chamber is liquid-tight by enclosing with one or more lids, said enclosure being liquid-tight.

In an embodiment, the chamber lid or lids are disposable.

In an embodiment, the lid or lids are attachable to the chamber by magnets or by mechanical pressure or mechanical fasteners.

In an embodiment, the chamber is comprised in a disposable capsule.

In an embodiment the chamber comprises a chemical or biological marker.

In an embodiment, the chamber comprises a needle for obtaining body fluids into the chamber, in particular a needle detachable from the chamber.

In an embodiment, the chamber comprises one or more mirrors for reflecting the light from the light source through the element to be characterized to the spectrometer, in particular the mirror or mirrors being attached to the chamber lid or lids.

An embodiment comprises one mirror in the chamber, said mirror being arranged distal to the optical device to reflect light back to the optical device, and comprising one mirror coupled to the optical device said mirror being arranged to reflect light back to the element to be characterized.

An aspect of the disclosure is an optical system for correlating, for parameter quantification, a recorded light spectrum with pre-obtained spectral bands for each parameter to be quantified, which comprises a plurality of light sources for emitting light onto the element, a plurality of spectrometer inputs for recording the spectrum of light, and a data processing module configured to select for the spectrometer, among the plurality of spectrometer inputs, the input or inputs which maximize the parameter quantification correlation with the pre-obtained spectral bands.

In an embodiment, the optical device is a bracelet.

In an embodiment, the disclosed light source and spectrometer are arranged to measure transmittance or reflectance.

An embodiment comprises a focusing lens for focusing the light from the element to the spectrometer at a specific distance within the element to be characterized.

In an embodiment, the light source is a bulb, led diode or laser diodes.

In an embodiment, the spectrometer comprises a CCD sensor.

An embodiment comprises a temperature sensor for measuring the temperature at the light source and/or at the spectrometer.

In an embodiment, the parameter is one or more of the following: in urine, saliva, whole blood or blood serum sample, or in non-invasive in-vivo skin-contact to blood vessel or adipose tissue: glucose, urea, creatinine, ALT, AST, cholesterol, triglycerides, uric acid, ALP, K, Na, Cl, Ca, amylase, total protein, micro-albumin, hemoglobin, erythrocytes, mean corpuscular volume, leukocytes, platelets, troponin, and/or myoglobin.

In an embodiment, the parameter is one or more of the following: probabilistic findings of intermediate diagnostic relevance of diabetes mellitus, renal insufficency; hyperuricemia; hepatic insufficiency; inflammation; and/or dyslipidemia.

In an embodiment, the optical system is for use in medicine, in particular for medical parameter characterization of an element of body fluid or tissue.

An embodiment comprises a remote data connection from the optical device to the data processing module, wherein the data processing module is located remotely from the optical device.

An embodiment comprises a local data connection from the optical device to the data processing module, wherein the data processing module is located at the optical device.

It is also disclosed the method or methods of operating the optical system comprising the method steps as referred above.

In an embodiment, the element to be characterized is human, mammalian or non-human animal, for use in medicine or in veterinary.

The above described embodiments are combinable.

GENERAL DESCRIPTION

Previous disclosures do not provide a simple, easy to use, modular, magnetic plug-in/plug-out probe system with compact optics in order to be easy to use by users in the determination of clinically relevant parameters in body fluids. For example, U.S. Pat. No. 7,688,440B2 and U.S. Pat. No. 7,524,671B2 present a system using test strips for blood analysis for Raman measurement, not solving the issue of direct blood measurement nor the modularity as the plug-in/plug-out system presented for the several types of probes. Modularity is extremely useful for measurement between different patients or even if one patient needs several different body fluids to be analyzed. The requirement of test strips is also disadvantageous.

GB2489717A presents a reflectance system with emitter and detector inserted in the probe, US2012/0035442A1, U.S. Pat. No. 6,064,897, U.S. Pat. No. 7,330,746B2, EP1620002B1 presents a systems consisting of fibreoptics probes for reflectance measurements. Moreover, these systems present the major disadvantage of small light pass lengths throughout the sample (one or double path length, depending on configuration), limiting the previous disclosures solely to the quantification of metabolites present in higher concentrations (g/l to mg/l range).

The present disclosure presents, among others, two transmittance probe designs (capsule and micro-needle) that are not only modular, but their configuration also maximizes the light path length due to its internal reflection surface, angular input/output of light, which increases namely up to the $10^{th}$ power the system sensitivity and high resolution of spectral interference pattern lines (Beer-Lambert's law).

The disclosure, namely of the probes and the overall system, is applicable to transmittance, reflectance or Raman modes of operation, with simple adaptations if necessary.

The high-sensitivity and resolution of the biophotonic signal recorded by the present disclosure, in particular, creates a new way on how to relate spectral information against the metabolite information in samples provided by an analytical chemistry lab. Previous systems vary in sophistication, but all assume the spectra as continuous, and therefore, quantification is done by: i) direct ratio at one wavelength (EP1620002B1), or ii) by the means of standard state-of-the-art chemometric and pattern recognition techniques (U.S. Pat. No. 6,167,290, U.S. Pat. No. 7,330,746B2 and U.S. Pat. No. 8,013,991B2). The present disclosure uses a different approach to cope with high-resolution signal that is provided by the biophotonics operating system.

These aspects of the present disclosure permit the measurement of practically all types of clinical relevant parameters in chemical analysis (for example electrolytes, metabolites, enzymes, carbohydrates, proteins and its subunits, lipids, identification of cells and determination of their numbers) and parameters useful as intermediate findings of diagnostic relevance (e.g. indexes probabilistically linked with analytical parameters which in turn are known to be linked with specific clinical situations). It is not envisaged that the present system may diagnose clinical situations, but it is indeed possible to produce parameters (i.e. indexes, scores) that correlate the parameters with those of a pre-identified clinical situation. Interpretation of the actual parameter values for reaching a diagnostic will usually require the intervention of a physician. For example, a high level of a probabilistic parameter linked to uric acid analytics may indicate hyperuricemia, but this in itself does not represent a medical condition though it can be indicative of specific medical condition or conditions.

Similarly, the high-sensitivity and resolution of the signal is associated with a biophotonic operating system (herein referred as BOS), that is in particular able to provide fine control on both light source and detector, in order to provide always, or as much as possible, the optimized acquisition conditions. Most of previous disclosures do not provide information on the biophotonics operating system.

Moreover, in order to facilitate the production of this system in large numbers, the biophotonic system in particular its operating system, BOS, is able to perform calibration transfer of all metabolites using only one internal standard. Current techniques involve the use of re-calibration and use of standardized samples during production or 're-calibration', to transport spectral information from a master to many client systems. BOS avoids such procedures, significantly reducing production costs, especially for low concentration metabolites generally measured by highly expensive or labour intensive analytical chemistry methodologies.

In this sense, previous disclosures are not able to achieve a holistic, multi-scale nature, and only provide a limited number of metabolite quantification. An example of the current status of the technology can be assessed in U.S. Pat. No. 7,330,746, U.S. Pat. No. 566,956, U.S. Pat. No. 4,890,619, EP1620002B1, U.S. Pat. No. 6,167,290, U.S. Pat. No. 6,064,897, GB2489717A, U.S. Pat. No. 7,524,671B2, U.S. Pat. No. 7,688,440B2.

The current disclosure provides a system to overcome the previous limitations, allowing point-of-care bio-photonic real-time, 'in-vivo', non-invasive, non-destructive metabolism monitoring and clinical parameter findings of diagnostic relevance.

One of the main objects of the present disclosure is to provide a biophotonic system that overcomes the state-of-the-art limitations, so that it can effectively provide a real-time, non-invasive, non-destructive monitoring of a wide spectrum of relevant chemical parameters for clinical findings of diagnostic relevance and monitoring based on spectral fingerprinting at the point of care. This optical bench compactness and miniaturization is namely due to the all-in-one plug-in/plug-out probe attachment system that allows to assemble in a small device all the combinations of transmittance, reflectance and micro-needle measurements. Furthermore, an embodiment is comprised of a cpu and storage unit, battery, opto-electonic system adaptable for both standard or stokes/anti-stokes shift scattering spectroscopy.

The present disclosure also provides modular, plug-in/plug-out, sterile, re-usable optical probes, especially designed to maximize the light path to provide high-sensitivity to obtain full spectral characterization and fingerprinting of low concentration metabolites. Further, the design of transmittance, reflectance and micro-needle probes based on magnetic or pressure/mechanical attachment, provides the user a flexible and fast way of performing the measurements in several individuals/patients with sterile safety, providing the holistic high-throughput characterization and clinical findings of diagnostic relevance of large populations.

Embodiments also comprise a biophotonics operating system (BOS), that allows the system to function properly and in some embodiments, enhanced its performance. The BOS in particular takes care of: i) states of the opto-electronic components (light sources, spectrometer, probes); ii) optimizes the spectra acquisition parameters of high-sensitivity and high-resolution measurements; iii) re-calibrates the system at each measurement for non-biased data; iv) performs pattern recognition to the spectra fingerprint to check its quality and integrity at each measurement; v) pre-processes the information, by extracting the relevant energy excitation orbitals, and correlates the observed spectral fingerprint to the samples metabolic composition and clinical findings of diagnostic relevance. This information is stored at local and/or remote database. Furthermore, it overcomes the limitations of spectral information transfer with the direct use of a standard probe and transfer algorithms built in the BOS, allowing low cost mass production of the present embodiments.

In summary, a full panel of analytical chemistry measurements of a wide spectrum of parameters (including eletrolytes, metabolites, enzymes, proteins and its subtypes, lipids, cells) is possible at the point-of-care, with extremely high efficiency and accuracy.

Overall, for a wide spectrum of parameters in blood, serum, urine and tissues, this device is accurate when compared to standard measurement techniques. Noticeably, a full spectrum panel of parameters of diagnostic relevance can obtained almost immediately, without the long waits for results to return from centralized laboratories.

Also being able to measure a wide range of parameters in a single shot approach, this disclosure serves as a mobile analytical chemistry laboratory that is highly cost-effective to produce and operate.

Analysis of parameters in the blood/serum/plasma represent the majority of the biological matrices sampled for bioanalysis. Yet, for this there is the need for vein catheterization and repeated blood sampling (namely in patients with chronic disease). Fortunately, the current disclosure works with a simple blood sample, in particular a drop obtained from a finger pin-prick; it is also prepared for the analysis of other fluids (such as urine, saliva, sweat or tear film) that do not need any invasive procedure. Furthermore, some embodiments measure parameters from the human or animal body, blood vessels or other tissues, without invasive interventions, wherein merely skin contact may be required in some embodiments.

Therefore, the system is able to provide high-throughput holistic metabolite quantification, clinical states probabilities and provide the necessary information for the application of medical clinical algorithms for findings of diagnostic relevance at the point of care.

An advantage of the present disclosure is the possibility to produce frequent body parameter quantification, e.g. without requiring frequent and/or large blood samples.

Another advantage is that, by acquiring and storing historical spectra of subjects, unknown parameters at the spectrum acquisition dates can be back-traced by re-correlating previously acquired historical spectra against the new parameter correlated spectral bands. This way, a discovery of a new parameter of relevance to subject health can be quickly applied to historical data.

In an embodiment, a point of care photonic system comprises: a simple, all in one, magnetic or pressure/mechanical attachment system with a modular transmittance, with magnetic or pressure/mechanical attachment, window and sterilization capability; a modular diffusive reflectance probe, with focusing lenses to the desired distance to perform tomographic spectral measurements; micro-needle for direct measurement of body fluids, with magnetic attachment;

A handheld and benchtop miniaturized system comprises cpu unit with communications systems (wireless and cable), display, keyboard, lightsource (typically 200-2500 nm continuous, e.g. lasers), spectrometer detector, and a power source, in particular a battery.

In an embodiment, a probe magnetic or pressure/mechanical plug-in/out system comprises: a simple attachment system for fast plug-in and plug-out of optical probes used in measuring biofluids.

An embodiment comprises a modular, plug-in, sterile, long path light length transmittance probe.

An embodiment comprises a modular, plug-in, sterile, long path light length transmittance micro-needle probe; micro-needle probe for minimal invasive measurement of body fluids, magnetic plugin system, channels to the measuring chamber.

An embodiment comprises a modular, plug-in, sterile, long path light length reflectance probe, with variable focus point; micro-reflectance probe, all in one, plug-in system, lenses system for variable focus point, in particular between 0.5 to 12 mm deep.

An embodiment comprises a spectroscopy operating system comprising spectrometer basic operations of quality control, optimized spectra acquisition, super-resolution, pattern recognition, high-end calibration, databases connections.

An embodiment comprises automatic spectral information transfer between devices in order to allow large production.

An embodiment comprises algorithms used in this process of automatic transfer of information between device systems without the need of reference samples or re-calibration.

An embodiment comprises monitoring of body fluids in samples.

An embodiment comprises the determination of probabilistic parameters of clinical states.

An embodiment comprises clinical algorithms for point of care findings of diagnostic relevance.

An embodiment comprises high-throughput population findings of diagnostic relevance.

The above described embodiments are combinable.

BRIEF DESCRIPTION OF DRAWINGS

The following figures provide preferred embodiments for illustrating the description and should not be seen as limiting the scope of the disclosure.

FIG. 2a shows a transmittance probe; FIG. 2b presents a micro-needle probe; and FIG. 2c shows a transmittance probe.

FIG. 5 shows an example of spectral information transfer.

DETAILED DESCRIPTION

Figure 1A:
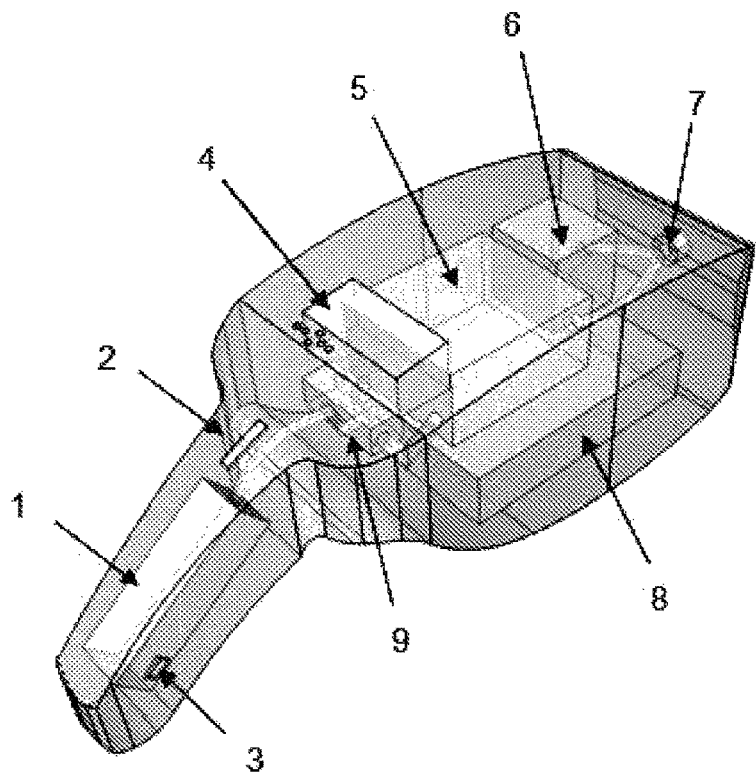
FIGS. 1a and 1b present the 3D view of the handheld and benchtop photonic system, with all the components, how these are assembled and connected to perform the present disclosure.
Figure 1B:
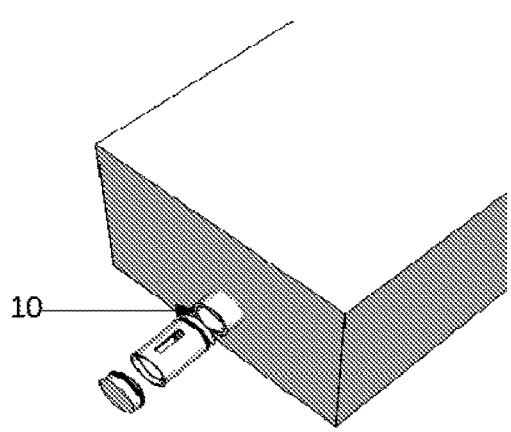

An embodiment of the modular point-of-care photonic system is presented in FIG. 1. This figure presents the handheld system and, in detail, the plug-in/plug out magnetic system, where sterile probes can be directly attached. The system is comprised of: 1—miniaturized personal computer (ram memory, flash disk, wireless communications, usb connection, cpu); 2—micro usb hub; 3—usb (recharge and connection); 4—LCD display and control; 5—Light source (led, light bulb or laser diode); 6—spectrometer; 7—magnetic plug-in/plug-out system; 8—Optical bench (connecting fibre optics); 9—Lithium ion battery; and 10—fast magnetic or pressure attachment for modular probes (reflectance, mini-needle and transmittance). The fast magnetic attachment system possesses the correct polarity in order to attract the probes or pressure tips to ensure perfect plugging as possible. Any type of mechanical fastener or mechanical coupling may also be used, mechanisms such as rotate-to-lock, clip-to-lock, slide-to-lock, among others.

Figure 2:
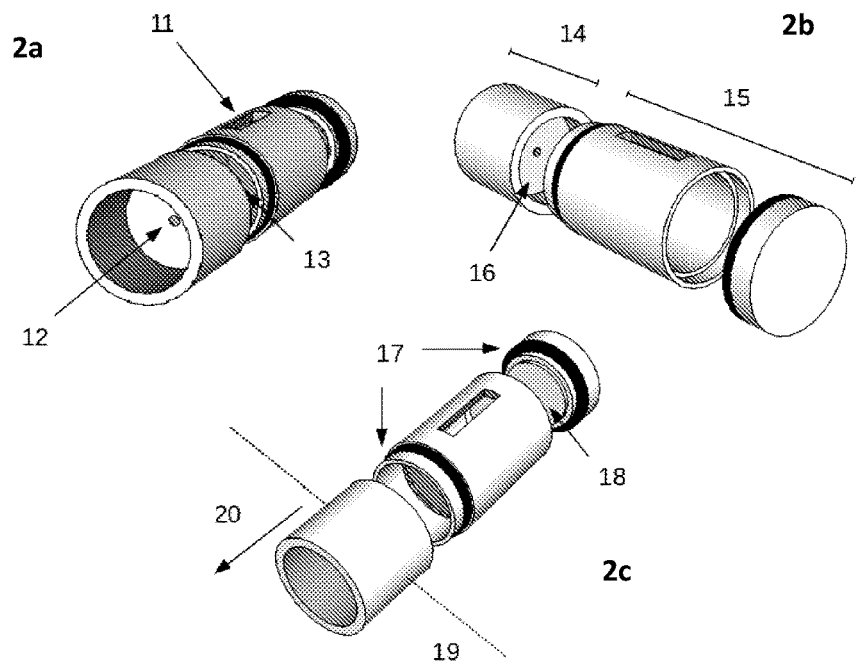
FIG. 2 presents the plug-in/plug-out system for a chamber and corresponding attachment probes.

All probes and the attachment system are preferably made of surgical grade steel or alternatively plastic for disposable kits. FIG. 2 shows an embodiment of a transmittance probe. This probe is designed so that the light enters a window (12) and passes through a glass (13) and through the samples. The optional misalignment of the input and output fibre in the window (12, 16) is purposeful such that light will be forced to be reflected inside the chamber a large number of times, so that the light path is significantly increased, and as a consequence, also signal sensitivity. Furthermore, as absorbed light is re-emited in all directions, a large proportion of it will escape through the top exit hole, and not enter the reception fibre slit, greatly increasing the difference between the emitted light and sample spectrum fed back to the receiver, and thus, sensitivity. The liquid samples are put inside the chamber in particular by the hole (11). The fast attachment occurs preferably due to the magnets, o-rings or pressure plug (17), attaching sections (14) and (15). The mirror (18) may also be detachable from the main part of the chamber for e.g. better sterilization and avoidance of cell or calcium deposits. Furthermore, (19) describes the axis of the attachment system, and (20) the direction. The chamber volume is usually less than 1 ml.

The attachment of the probe with the chamber to the main device can be alternatively carried out by mechanical pressure or mechanical fasteners, as mentioned above.

Figure 3:
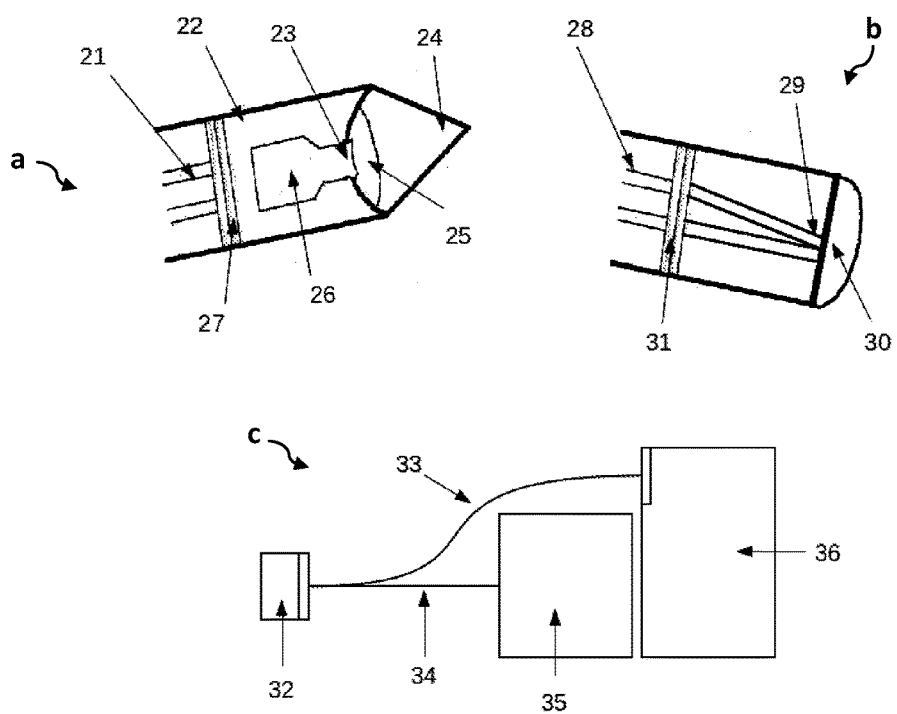
FIGS. 3(a) and 3(b) presents the internal optic system to enable the plug-in/plug out system using uv-vis-nir bulbs or led diodes, and laser diodes, respectively.
FIG. 3(c) presents the spectroscopy operating system basic components.

FIG. 3(a) presents an embodiment with micro-needle and an embodiment of diffusive reflectance probes, as well as, the optical bench. The micro-needle probe is composed of: (21) optical bench; (22) steel capsule or other suitable material, in particular plastic for disposability; (23) microchannel; (24) puncturing tip; (25) mirror(s), in particular one mirror, distal from the main system; (26) internal chamber and opening; (27) fast plug-in/plug out system in particular equal to any of the previously described for the transmittance probe. After puncturing the skin, a small drop of blood is channeled into the measuring chamber, where the measurement is taken. In particular, the needle or puncturing part (24) of the probe is connected to the internal chamber (26) through an opening in the distal mirror (25).

An embodiment of the transmittance probe 3(b) comprises of (28) fibre optics; (29) illuminating and centre capture fibre optics; (30) focusing lenses; and (31) fast plug-in/plug out system preferably equal to any of the previously described for the transmittance probe. This probe measures the light reflected from the specific focus point inside a tissue. Different lenses can provide different focusing reflectance distances for spectral measurements at pre-determined depths of samples or body parts with no invasion of the body by pointing (e.g. from a distance, usually small distances, limited by the sensitivity of the system), in particular touching, at the surface (skin, in most situations, but other surfaces are possible, namely different mucosa). Focusing mechanisms provide the ability to perform automatic scanning characterization at different distances.

Figure 12:
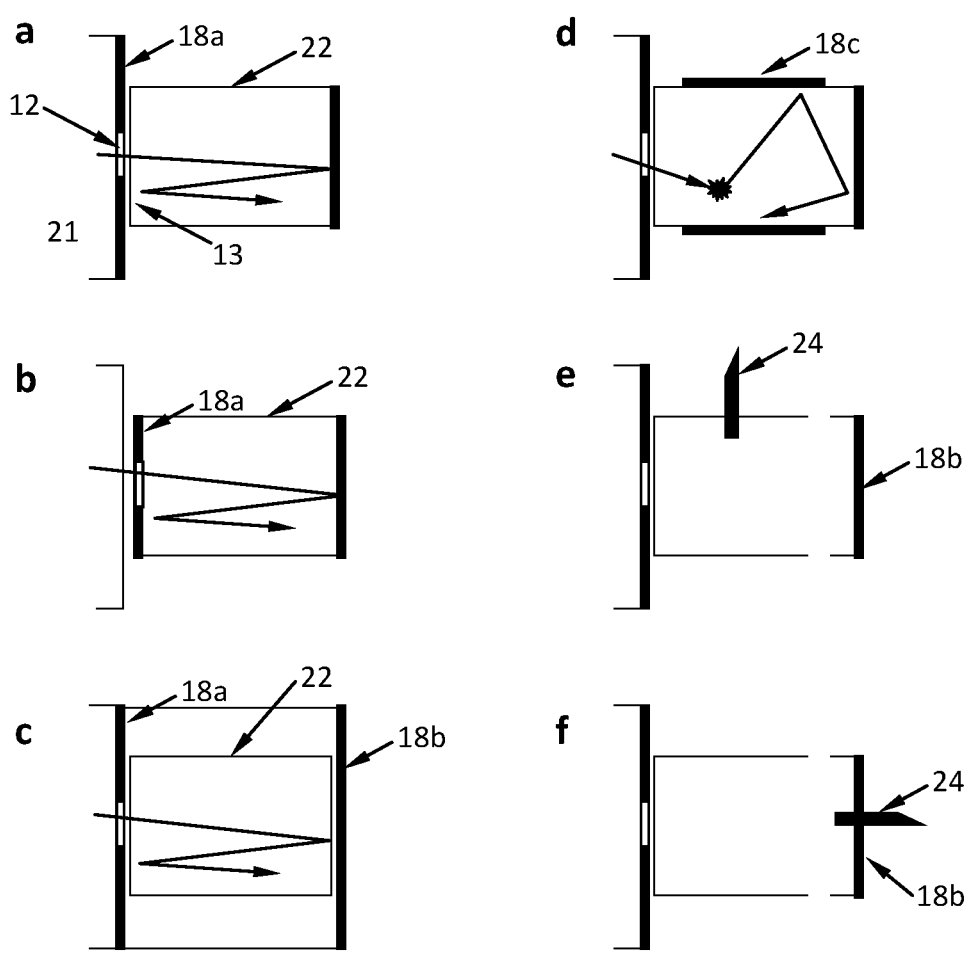
FIG. 12 shows a schematic drawing of embodiments for a probe, in which a capsule comprises a chamber for receiving a sample.

An aspect of the disclosure is the probe used with the optical system. FIG. 12 shows additional embodiments for the probe, in which a capsule (22) comprises a chamber for receiving the sample.

In an embodiment (a), the optical bench (emitter and receiver) transmits/receives through a window (12) in a mirror (18a) rigidly coupled to the optical bench part of the system. The capsule (22) comprises a transparent window (13) in the part proximal to the optical bench, that allows the emitted light to pass through to the chamber and to return back to the receiver. A second mirror (18b) is provided in the capsule distal to the optical workbench. This way, the emitted light is able to reflect multiple times between the mirrors before being reflected back to the receiver and thus amplify the signal received. Preferably, the emitter, receiver and/or mirrors are aligned such that light will travel between emitter and receiver such that the number reflections are maximized. The second mirror (18b) being in the capsule has the advantage that light will not pass through the capsule wall when being reflected by this second mirror (18b), thus improving the signal quality.

In an embodiment (b), the first mirror, closest the workbench (18a), is alternatively located in the capsule (22) in the part proximal to the optical bench. This has the advantage that, compared to the previous embodiment, reflected light at the first mirror does not pass multiple times through a capsule wall (13) improving signal quality. If light passes multiple times through a capsule material the signal may be distorted by the capsule material (this may not be possible to be compensated by software). It has the disadvantage that construction is not as simple as for the previous embodiment and the cost of the capsule is higher, an issue if the capsule is disposable (not reusable).

In an embodiment (c), both mirrors proximal (18a) distal (18b) are provided coupled to the optical workbench, and the capsule (22) does not include any mirrors but simply transparent walls next to said mirrors such that light might be reflected from emitter to receiver multiple times through the sample. It has the advantage that construction is simpler, as compared to the previous embodiments, and the cost of the capsule is lower, an important advantage if the capsule is disposable (not reusable). It has the disadvantage that light passes multiple times through a capsule material (twice as much as embodiment 'a') and the signal may be distorted by the capsule material (even if this may be possible to partially compensate by software in some cases).

In an embodiment (d), the capsule may be provided with lateral mirrors (18c) relative to the reflection of the light path. This is usually an advantage in Raman modes of operation where re-emitted light (in all possible directions) is of interest.

For transmittance modes of operation, lateral mirrors are usually disadvantageous as re-emitted light is of no interest in this case—the absence or reduction of lateral reflection is of interest in that the embodiment promotes reflection of transmittance light (direction perpendicular to the lateral surfaces) over reflection of re-emitted light (all directions).

In an embodiment (e) the capsule is provided with a puncturing tip (24) for obtaining the fluid (for example, blood) sample into the chamber. Alternatively, instead of a puncturing tip, an opening may be provided, optionally closable with a lid. Alternatively, a part of the capsule wall may be puncturable, for example by a syringe, for receiving the fluid sample. Alternatively, the capsule wall comprising the distal mirror (18b) may be detachable for receiving the fluid sample. These options may be freely combined for providing multiple options to the user.

In an embodiment (f), the puncturing tip (24) is located at the capsule wall comprising the distal mirror (18b), said wall being detachable for receiving the fluid sample. This way the part of the capsule comprising the puncturing tip may be disposable, while the rest can be re-used. Alternatively, in another embodiment (e), the puncturing tip (24) is located in a capsule wall that does not comprise the distal mirror (18b), said wall of the distal mirror (18b) being also detachable for receiving the fluid sample. This way the disposable part does not include a mirror and the cost for re-use may be lower.

In an embodiment, the chamber of the capsule may be pre-provided with chemical or biological markers, for example genetic markers, such that the fluid sample mixes with said marker(s). A marker generally refers to a measured characteristic which may be used as an indicator of some chemical or biological parameter. This way, specific parameters which cannot be obtained through the spectra received from the sample, can now be detected as long as said markers make apparent in the recorded spectra said parameters. For example, it is advantageous to provide specific colouring markers able to provide a significant spectrum change on the presence of elements which would normally be transparent to the light frequencies herein used.

The internal optical bench is, in an embodiment, composed of the (32) the fast plug-in/out system with to each two internal fibre optics are linked; (33) is the fibre optics that conducts the light from the light source (36); and (34) the fibre that conducts light into the spectrometer (35).

Based on this disclosure, a biophotonics operating system (BOS) is also disclosed, such that with practically any type of dispersive spectrometer, it is capable of performing the following: i) system diagnosis initialization, such as checking and managing the temperature of the light source and spectral recording conditions; ii) using a reference for performing the diagnostic of the optical properties of the spectrophotometric system; iii) apply the necessary corrections of the spectrum compared to the reference spectrophotometer; iv) automatic transfer of calibrations between different chemical and metabolic spectrophotometers with different configurations and optical components; v) automatic transfer of calibrations of discrete features, ratings and discriminating between spectrophotometers with different settings and different optical components and vi) diagnosis of the operating system in real time spectroscopic and their operational limits under correction signal.

The current approaches make unnecessary the comparison between different spectrophotometers, of the same or even different manufacturers, as well as the comparison of the same spectrophotometer with different combinations of optical elements and various light sources; making complex development and implementation of the diagnostic equipment well as universal calibration multi-varied in a large scale. To illustrate this problem, FIG. 5A(c) shows the reflectance spectrum reference with: i) reflectance spectrum with the source of mercury lamp A and B, ii) a source of tungsten C and D. FIG. 5B presents the spectral conversion for the tungsten light bulb with the source and spectrometers with different resolutions and optical components.

Several authors have developed methods to perform the re-calibration of compositional forecasting models based on a master spectrophotometer, and which 'used as the standard method for estimating the chemical composition of the samples and their subsequent use in calibration of 'cloned' spectrophotometers'. Given the need for sample handling, this process is quite similar to the re-calibration of analytical laboratory equipments, where the quantification is effected in this case by a master spectrophotometer to minimize costs by other analytical equipment.

The manipulations involve analytical costs of human labour, and re-calibration provides a new model for a spectrophotometer different from the original, and there is a true conversion of spectral information between spectrophotometers. The need for successive re-calibrations due to degradation of optical systems and/or changes in the configuration of the equipment makes it difficult to generalise and long-term reliability of the equipment forecasting of chemical and metabolic imaging. Furthermore, the inability to compare spectra between different devices, makes it impractical the comparison between chemical and metabolic images or composition for clinical diagnostic between different spectrophotometers. Such handicaps, do not allow to automate operations, such as operational diagnostics of the optical components or even planning a computerized maintenance plan, because, for example, automated procedures are not able to differentiate between normal and acceptable sensor drift and sensor malfunction.

This disclosure in particular combines the development of an operating system with artificial intelligence and an adaptation probes transmittance and reflectance using the knowledge of the opto-electronic processes occurring in the various components of the spectrophotometer, in order to automate the following operations: i) making the system diagnosis of initialization, optimization of vesting conditions and check the temperature of the emission source; ii) system Diagnostic reference—to make the diagnosis spectrophotometric properties optical system; iii) correction universal spectrum in relation to the reference spectrophotometer; iv) automatic transfer of calibrations between different chemical and metabolic spectrophotometers with different configurations and optical components; vi) diagnosis of the operational status of the system in real time spectroscopic and their operational limits under correction signal; vii) use the above information to operate the spectrophotometer always, or as much as possible, under optimum conditions of operation and proceed with his plan optimized maintenance and repairs.

FIG. 3(c) presents the operating system basic components.

Figure 4A:
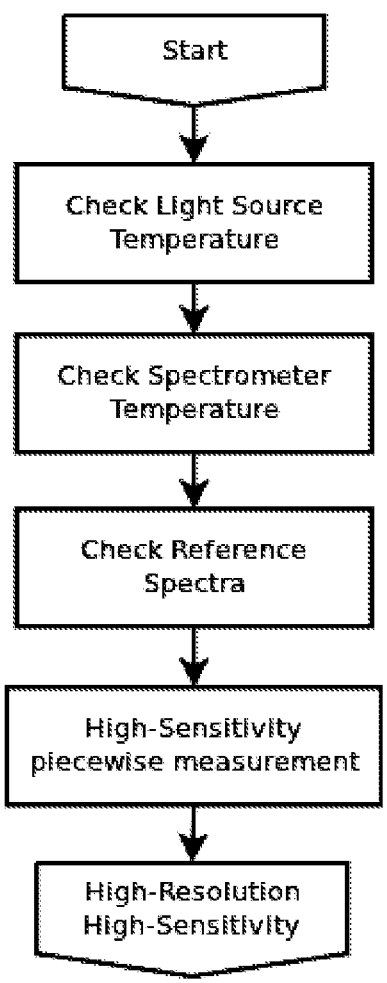
FIG. 4A shows the basic operation procedure for recording a spectra.
Figure 4B:
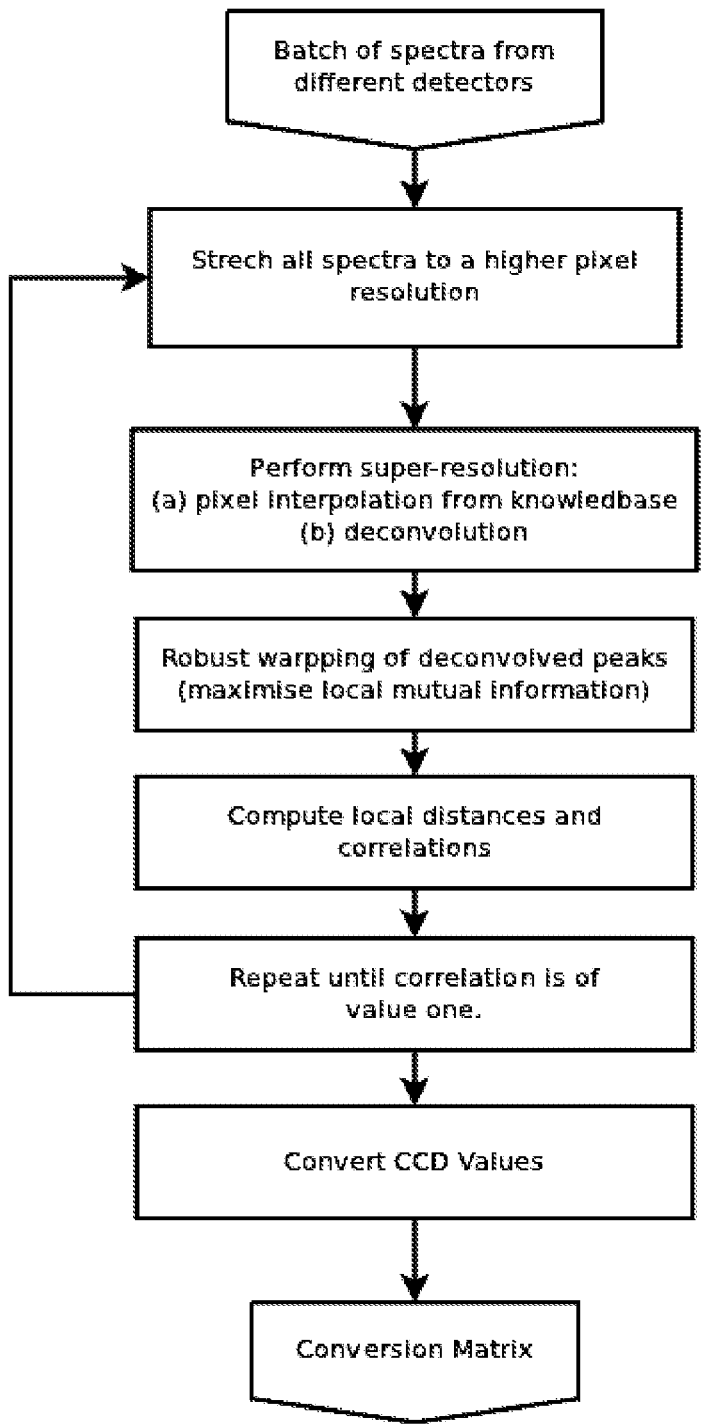
FIG. 4B shows the procedures for performing the information transfer between different types of optoelectronic systems.
Figure 4B:
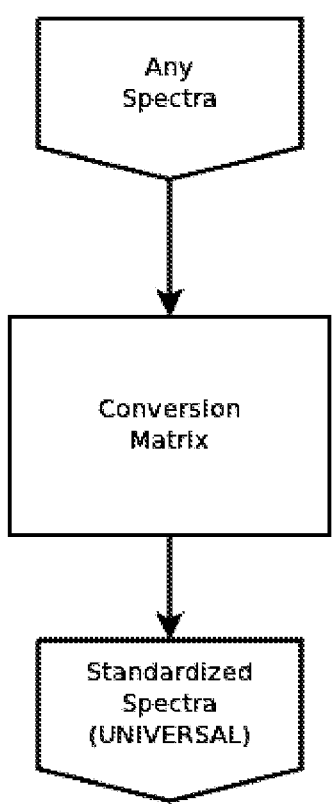
Figure 4B:
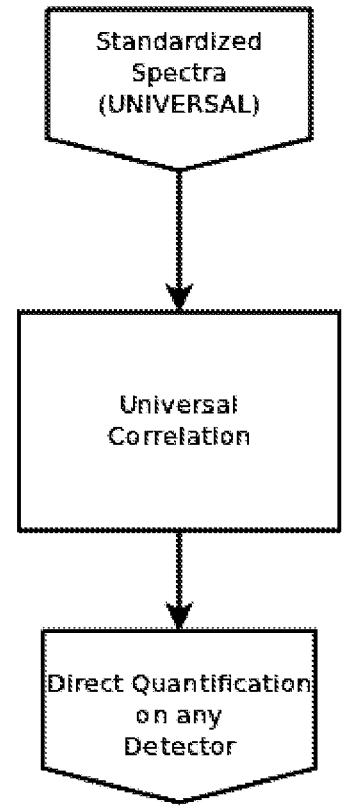
Figure 4C:
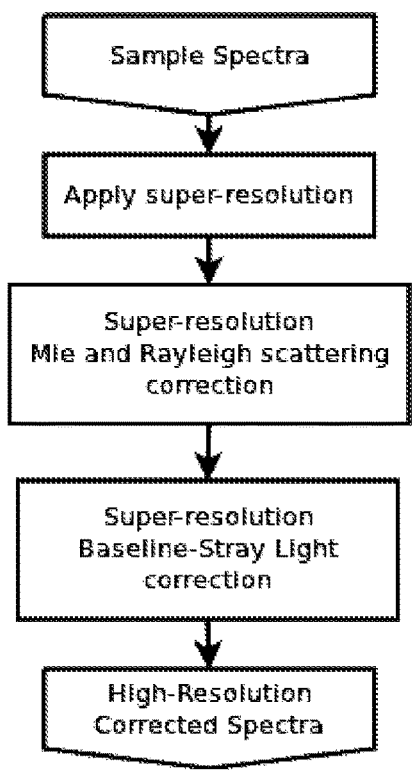
FIG. 4C shows how the system corrects and predicts the metabolic composition from a recoded spectra.
Figure 4C:
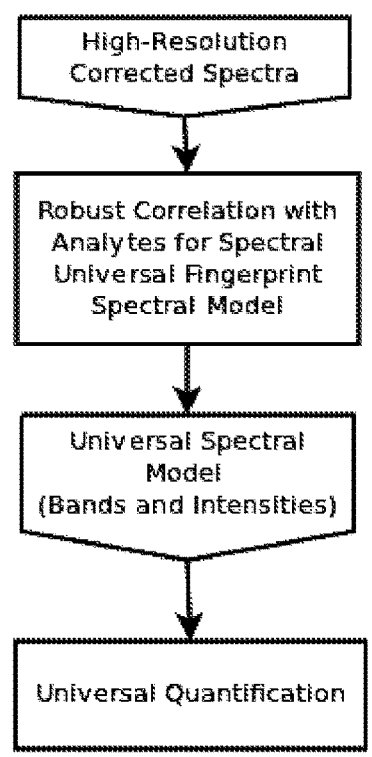

FIG. 4A shows the basic operation procedure for recording spectra; FIG. 4B shows the procedures for performing the information transfer between different types of optoelectronic systems; and FIG. 4C shows how the system corrects and predicts the metabolic composition from a recorded spectra.

The spectrum measurement procedure is automated as follows:

Check light source temperature: light source preferably has a temperature sensor, namely a miniature thermocouple, that allows to check if the optimum operational temperature is attained. The temperature is critical for a stable spectrum emission, either from a led diode, light-bulb or laser diode. If the temperature is inside the optimum interval, the system proceeds; if not, the system holds and waits until the condition is satisfied, optionally producing an alert to the user.

Check the detector temperature: sensor, in particular CCD, temperature is critical for high-resolution and sensitivity, due to non-linear effects on sensitivity and signal/noise ratio. The CCD detector has, in an embodiment, an internal thermocouple to measure its temperature, and if this is above the threshold, a mini-fan is used to cool it, if is below, the system proceeds; if not, the system holds and waits until the condition is satisfied, optionally producing an alert to the user.

Check the reference spectra: in order to check if measurements are reproducible, the system takes a reference spectrum or spectra of e.g. PTFE (Polytetrafluoroethylene) present in capsule tip, and runs the method in FIG. 4B(a), to compare the high-resolution spectrum or spectra with the database; if ok, proceeds; if not, the system holds and waits until the condition is satisfied, optionally producing an alert to the user.

Perform spectra recording, in particular by performing piecewise measurement: for any sample, the system chooses an optimal wavelength window, and optimizes both integration time and light intensity, so that the recorded spectra in that window is always, substantially, or as much as possible, inside the optimum sensitivity and linear region of the detector; the window moves to a super-imposed interval, and repeats this procedure until all the wavelength range of the detector is covered or alternatively captures multiple intervals, not subsequently superimposed, but taken as a whole superimposed with other intervals or bordering other intervals, such that all wavelength range is covered. The final spectrum is composed of all the aligned segments, with the signal intensity corrected taking into consideration the integration time and light intensity.

The above described piecewise recording at the spectrometer is generally applicable to spectrometer readings, can be used with any spectrometer recording method, not being limited to biophotonic applications.

Constituting input data, the recorded spectrum should have sufficient frequency width to be able to determine the parameters being characterized by the system.

The final composed spectrum or spectra is recorded into the system database. The system preferably records at least 10 optimized spectra for further processing.

Metabolic quantification procedure—after the spectra are recorded, the following procedure produces, in large-scale, the proposed equipment and high-resolution metabolite quantifications without the need of calibration transfer, using the following spectral information transfer method (see FIG. 4A (a) for illustration purposes):

Stretch the reference recorded spectra to a higher pixel resolution (preferably always greater than three times, using interpolation for the missing data);

Spectrum peak resolution is essential for the extraction and quantification of spectral bands in complex biological samples, such as blood, urine or human tissues. Dispersive spectroscopy technology optical resolution is limited by the slit size and grating grooves/angle. The combination of these two components with the internal optics, provide the specific resolution of a dispersive spectrometer under the Rayleigh criterion of band pass resolution (Lerner, 2006). The observed spectrum of any sample is therefore the convolution of the light signal and the optical bench apodization functions, that smooth spectral bands (Burns and Ciurczak, 2001). The lesser resolution, the higher the effect of the apodization function and vice-versa. This effect can be mathematically corrected by the inverse operation, the deconvolution of the apodization function from the observed signal, such as using the box-car, triangle or Gaussian point-spread functions as apodization functions for the spectral optics (Kauppinen and Partanen, 2001).

When using a lower resolution spectrometer, it is possible to convert the spectral signal beyond its original spectral resolution by deconvolution and local regression against the signal of high-resolution equipment. That allows the direct mathematical conversion between spectroscopic signals between different machines without the risk of over or under deconvolution, as the apodization effect is optimized by local regression against the higher resolution signal. These techniques are used to implement super-resolution spectral information transfer between spectrometers as follows.

Perform super-resolution to obtain higher spectral full width at half maximum (FWHM) than the optical limit:
use the spectral replicates to develop the interpolation model of the full pixel resolution by local regression;
perform deconvolution to resolve convolved information below optical resolution;

Interpolation involves local regression between known data points and this is commonly carried out by polynomial, spline, linear, sinusoidal, etc, functions.

Replicates are generally used being experimental repetitions so that the variability associated with the phenomenon can be estimated, being optional in the sense that a method may work with only one sample but with an increased error margin.

Perform local peak warping and compute distances between the reference spectra and the recorded spectra, and repeat local warping until the correlation value between the recorded spectra and reference spectra is above the threshold, in particular when the correlation is one, and if so, proceed;

Convert the spectra between spectrometer by a relational model, and store the relation ratios in a conversion matrix. This matrix can now be used to both stretch and convert directly any new spectra into a universal detector. The conversion matrix has a multiplicative conversion factor for each input and each output frequency. In particular, the conversion factor may be linear, consisting in both multiplicative and additive factors. In particular, the conversion factor may be multiplicative, consisting in a multiplicative factor.

The above stretching may occur either explicitly using the peak information as above which is preferred, or simply by other known techniques for function mapping, for example by randomly or uniformly segmentation of the spectra, and further iterative local expansion or contraction of the segments until a matching is obtained, without explicitly using peak information.

The above calibration procedure is thus able to provide a conversion matrix that fully calibrates a spectrometer against a reference spectrum. This calibration is thus able to adapt the system to different spectrometers (e.g. pixel count)

or different light-path elements (different spectrometer gratings introduce frequency and intensity shifts; different spectrometer slits introduce differences in resolution).

In this way, a second 'master' spectrometer is dispensed with, simply requiring a spectrum reference.

Another simpler calibration method can also be carried out, able to correct for variations in the materials within the light path, in particular in the window glass material or in individual capsule materials. It comprises taking a measurement, without the body element to be characterized, in particular of the empty capsule if present in the embodiment, and calibrating against a previously obtained spectrum reference measurement. For example, the thickness of the capsule material (affecting substantially all the spectrum) or colour of the capsule material (affecting part of the spectrum) can be thus compensated. This calibration is in particular a linear calibration for each frequency, thus simpler than the full calibration above. This simpler calibration does not require complex calculations and thus can be used more frequently than the previous calibration, for example every time a new disposable capsule is inserted, or immediately after the system being powered up, or before every measurement.

As any new spectrum is recorded, the following procedure is performed (FIG. 4B(b) and FIG. 4B(c)):

Use the conversion matrix to correctly expand and convert the spectra into standardized spectra;

This spectra is subjected to further pre-processing (explained in FIG. 4B), and afterwards (FIG. 4C).

Can be directly used using a direct correlation procedure between spectral bands and metabolites for direct quantification in any detector.

FIG. 5b exemplifies the measurement of a serum sample using two spectral information transfer between detectors of 0.54 nm and 2.87 nm optical resolution with a halogen-tungsten light source. FIG. 5b(a) presents the very significant spectrum differences between the measurement of the same serum sample. FIG. 5b(b) shows the converted spectrum and FIG. 5b(c) the direct prediction of serum glucose correlated between detector 1 and 2.

Universal metabolic quantification—metabolic quantification is performed by correlating extracted compounds spectral fingerprint, supervised by clinical analysis. In this disclosure, for purposes of illustrating the disclosure, we used the following number of samples: i) 10270 of blood serum; ii) 2730 of whole blood; iii) 3480 of urine; iv) a smaller sample of pulse vein measurements and v) a smaller sample of fat tissue biopsies. All comparative analytical chemistry quantifications were performed by the universal standard methods in a certified clinical laboratory.

It is also developed an universal spectral fingerprint database of metabolites present in biofluids and tissues.

These fingerprints, pre-obtained spectral bands, may be explicit, e.g as latent variables of a multivariate regression model, or may be implicit, e.g. as hidden variables of an artificial neural network.

Any suitable multivariable correlation or regression model may be used, but models that allow explanatory verifications of the results are usually preferred, e.g. a multivariate regression model.

Each of the samples used for quantification in the clinical analysis laboratory was subjected to recording of the spectra, and this spectra is used to build the universal quantification database according to the following procedure (FIGS. 4C(a) and 4C(b)):

Each of the recorded spectra may in particular be subjected to the super resolution procedure explained in the previous section in order to obtain a high-resolution spectra;

The high-resolution spectra is subjected in particular to both Mie and Rayleigh scattering correction; there are known methods for correcting for Mies scattering (where wavelength is smaller than particle size) and for correcting Rayleigh scattering (where particle size is smaller than wavelength) of the super-resolution signal;

The high-resolution spectra is subjected in particular to base line and stray light correction; there are known methods for removing a signal component which is constant across all frequencies (baseline) and for removing a signal component corresponding to known stray-light spectra (e.g. subtraction) of the super-resolution signal;

It is thus obtained the high-resolution corrected spectra in FIG. 4C(a) which carries over to FIG. 4C(b).

The resulting spectra is thereafter subjected to robust regression against the analytical results; from this robust regression analysis, results the extraction of the relevant bands for quantification of each metabolite, that is, the universal metabolite spectral fingerprint. This is used afterwards for direct quantification as presented in FIG. 4B(c).

As mentioned above, these fingerprint quantification bands may be explicit or implicit.

Figure 6:
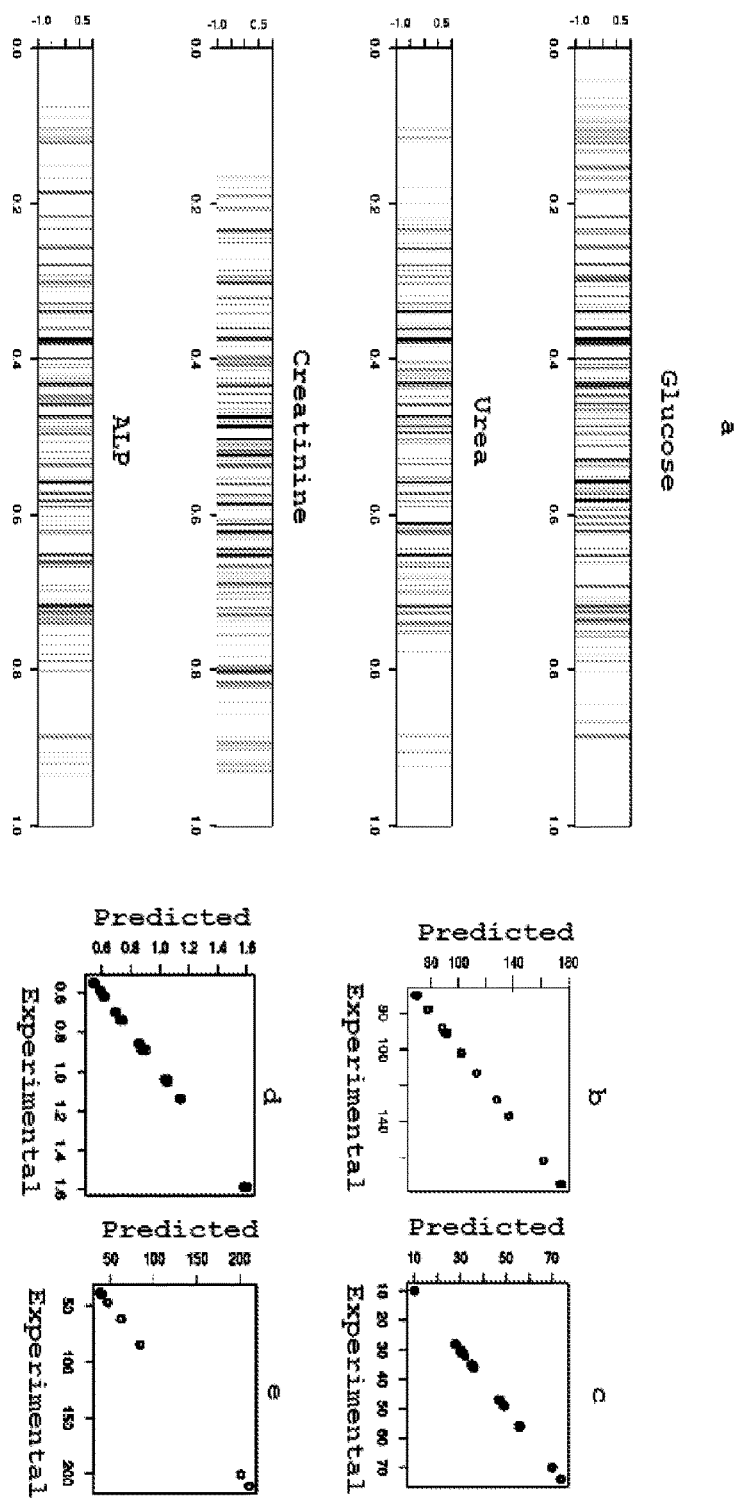
FIG. 6 shows an example of metabolite spectral fingerprint extraction and corresponding quantification for glucose, urea, creatinine and alkaline phosphatase (ALP).
Figure 7:
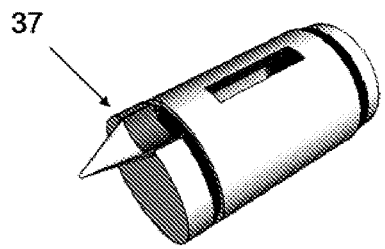
FIG. 7 shows a probe detail with micro-needle (37), showing the pin puncturing point and channeling of blood sample into measurement chamber.
Figure 8:
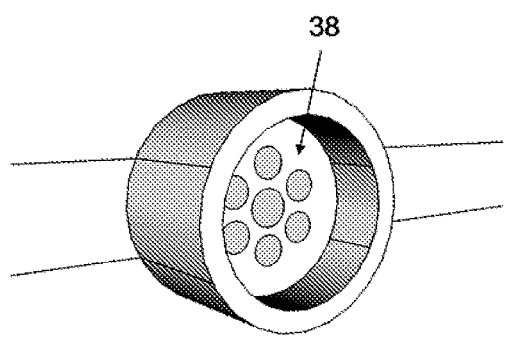
FIG. 8 shows a probe detail of the plugin attachment system (magnetic or pressure/mechanical) with the 6 illuminating (emitter) fibres and one reception fibre, in this particular case the emitter fibres surrounding the receiver fibre.
Figure 9:
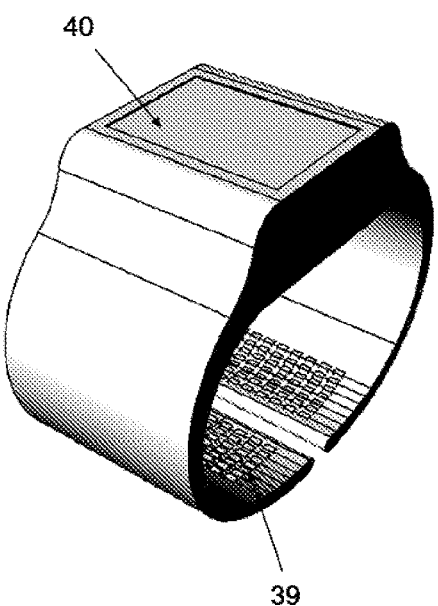
FIG. 9 shows a view of a personal photonic system, with the respective components, showing how these are assembled and connected to provide a wrist-held device: (39) sensor array and (40) results display/user interaction.
Figure 10:
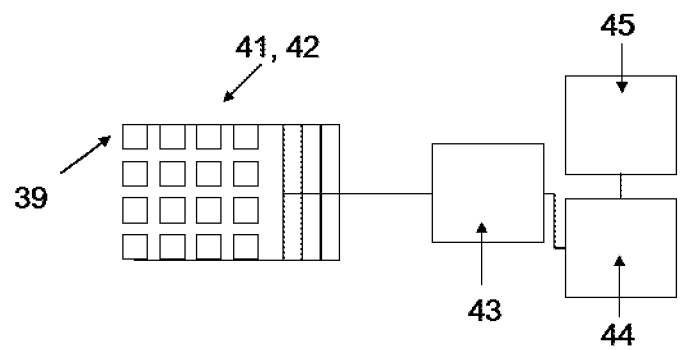
FIG. 10 shows a schematic drawing of the optical parts of the personal photonic system and how they fit together for proper function: (41) electric mount, (42) fibre optics; (43) spectrometer; (44) pc or data processing unit; (45) display/control.
Figure 11:
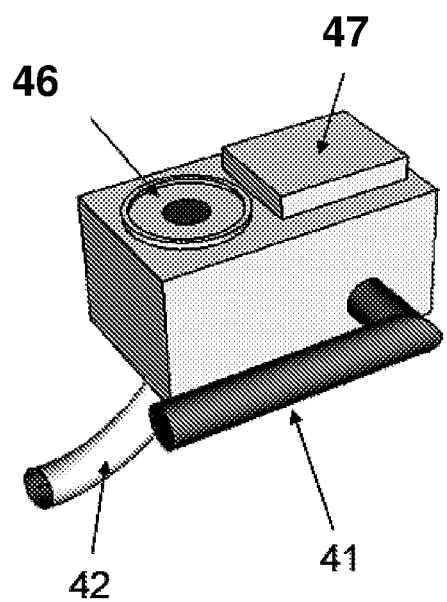
FIG. 11 shows a miniaturized sensor from the sensor array (39), comprising of: (41) power cables, (42) reception fibre, (46) miniaturized reflectance probe and (47) LED.

The present disclosure was applied to samples and tissues of human species, i.e. a warm-blooded mammalian animal, and the results are described and discussed. To exemplify the result of this procedure, FIG. 6(a) present the universal metabolite spectral fingerprint for glucose, urea, creatinine and alkaline phosphatase. The direct proportion of signal intensity of these bands provides the corresponding quantifications presented in FIGS. 6(b) to 6(e), respectively. Tables 1 to 3 show the blood serum, whole blood and urine metabolite quantification and correlation with spectral fingerprinting technique, respectively.

Table 5 presents the same approach for identifying the spectral fingerprinting probabilities associated with a clinical state, thus these probabilities constitute indexes which can be used as intermediate findings of diagnostic relevance.

Automatic spectral information transfer—conventionally, calibration or metabolic properties is effected against discrete standardized laboratory methods or sophisticated instrumental methods of analysis, such as HPLC, LC-MS, GC-MS and NMR. These laboratory methods involve a very significant investment in human resources, materials, consumables and time, since the databases calibration holistic. Thus, conventional unbiased calibration of uv-vis-nir spectra using chemomerics may take several years to be completed, cost analysis of thousands or millions of samples making its repetition economically unviable to be performed for each new equipment that is produced.

Traditionally, calibration transfer between spectrometers' done with recourse to standardization. A master spectrophotometer is used to measure and estimate the properties of standardization samples, these being subsequently used to re-calibrate the slave spectrophotometer (Ciurczak and Burns, 2001; Feudale et al., 2002). Similarly, the spectrum of the slave spectrophotometer can be used to determine the properties using the master model spectrophotometer, leading to skewed estimates, which are subsequently corrected mathematically relating the two predictions (generally linearly correlated, since the calibration models using multivariate linear). One consequence of these two methods is the loss of information relative to initial calibration, and when used in cascade leads to significant loss of information due to the propagation of statistic noise between cloned spectrometers; beyond which can lead to systematic introduction of errors due to errors or deterioration of preparation of samples of standardization and making the spectral databases obsolete.

To obviate this problem, others developed robust calibration methods (Woody et al. 2004; Wangdong et al. May 2011). A robust calibration involves the use of massive data and equipment, or judicious selection of representative samples of complexity existing in the original database. Assuming that these two criteria are achieved, the following methods are proposed: i) Two-step PLS (Forina et al., 1995), ii) S-PLS (Wangdong et al., 2011), iii) Canonical Correlation (Fan et al., 2008) iv) The PLS-(Woody et al., 2004), v) of reconstruction data (Warzel and Andrews, 1997; Hopke and Xie, 1999); vi) data fusion (Ni et al., 2010) and vii) neural networks (Despagne et al. 2000). The basic principle of all these methods is the fact that with sufficient samples representative of the variability of the system (hardware, accessories and biological variability), it will be possible to construct calibration models that are immune to sources of bias being transferred subsequently minimizing the recourse to standardization methods. However, during the process of transferring calibrations, these methods require that both devices are available at the same time and place, for the measurement sample transfer, which in case of equipment dedicated to acquisition spectra in an industrial environment or 'in-vivo' is impractical. For example, this method would require the existence of a master device always additionally, and does not solve problems of failure or deterioration of optical components, with consequent significant loss of information.

The standardization samples are usually chosen with the following properties: i) representative of calibration range (e.g. pure chemical compounds at different concentrations) and ii) durability standards (e.g. halon polystyrene) (Feudale et al. 2002). While prior methods attempt to deal with the effects of the components variance and statistical models closed, methods of standardization attempt to solve these problems relate the properties of spectrophotometers along the spectrum collected. The first existing patented method is that of "direct standardization" (Westerhaus and Shenk, 1991; Westerhaus and Shenk, 1996). This performs a linear relationship between the spectrum spectrophotometer master and slave, so that makes it possible to convert the spectra from any instrument slave to master, with the forecast made on the master model, respectively. In order to obviate problems nonlinear optical component (e.g. optical diffraction peaks and deviations) were introduced modifications and enhancements to this approach, such as direct standardization part (Wang et al. 1991, Wang and Kowalski, 1992) and its variations (Geladi et al. 1,999; Barring et al. 2001), where the spectrum is corrected linearly within a sliding window. Within this same philosophy, methods have been developed to carry out the standardization in the field of direct compression using wavelets, minimizing the effect of noise during the transfer of the detectors (Walzack and Massart 1997; Walzack et al. 1997).

All existing methods in the literature are based on statistical relationships between spectrometers (master and slaves), not taking into account the opto-electronic phenomena that affect the performance of different models of spectrophotometers with different components and accessories (Table 1) in particular the latest dispersive equipment with high spectral resolution and detection sensitivity.

The spectrophotometers produced by different manufacturers display different optical components (slit, grating, lenses, prisms and detector), and their users can utilize them with different sources of light emission, as well as fibre optics and probes. As it well is known, the spectral information of each device as well as its various configurations are unique, producing a spectral signature or spectral information individualized for each of the different equipments.

The current approaches make invalid the comparison between different spectrophotometers from the same or different manufacturers, as well as, the comparison of the same spectrophotometer with combinations of optical elements and various light sources; which turns impossible to implement a generalized strategy for the diagnostic equipment well as an universal calibration methodology that allows to mass produce calibrated spectrometers for metabolic quantification.

The present disclosure aims at also providing a solution to these matters.

Figure 5A:
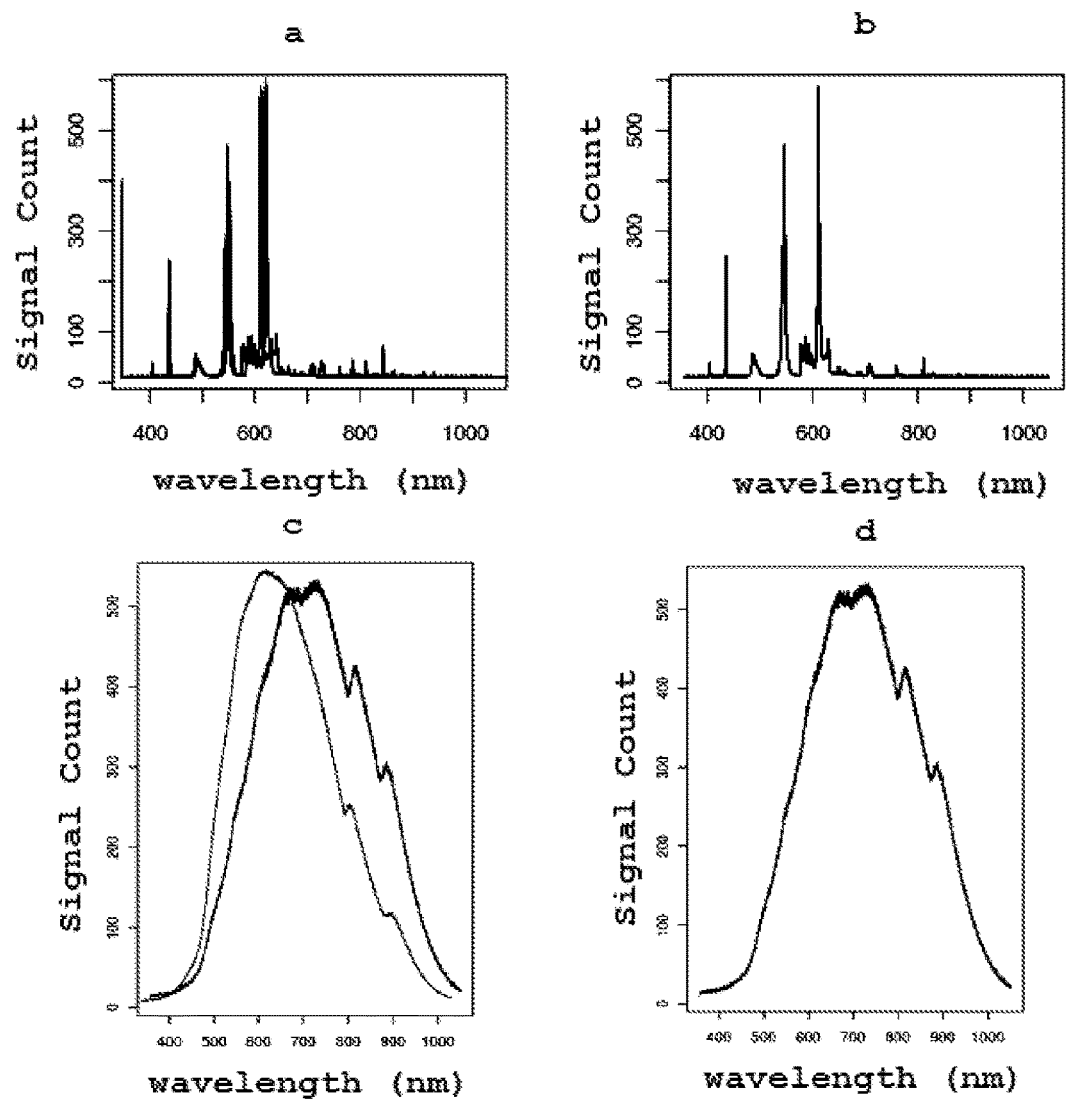
FIG. 5A shows an example of spectral information transfer between detectors of 0.54 nm and 2.87 nm optical resolution with a mercury reference light source.
Figure 5B:
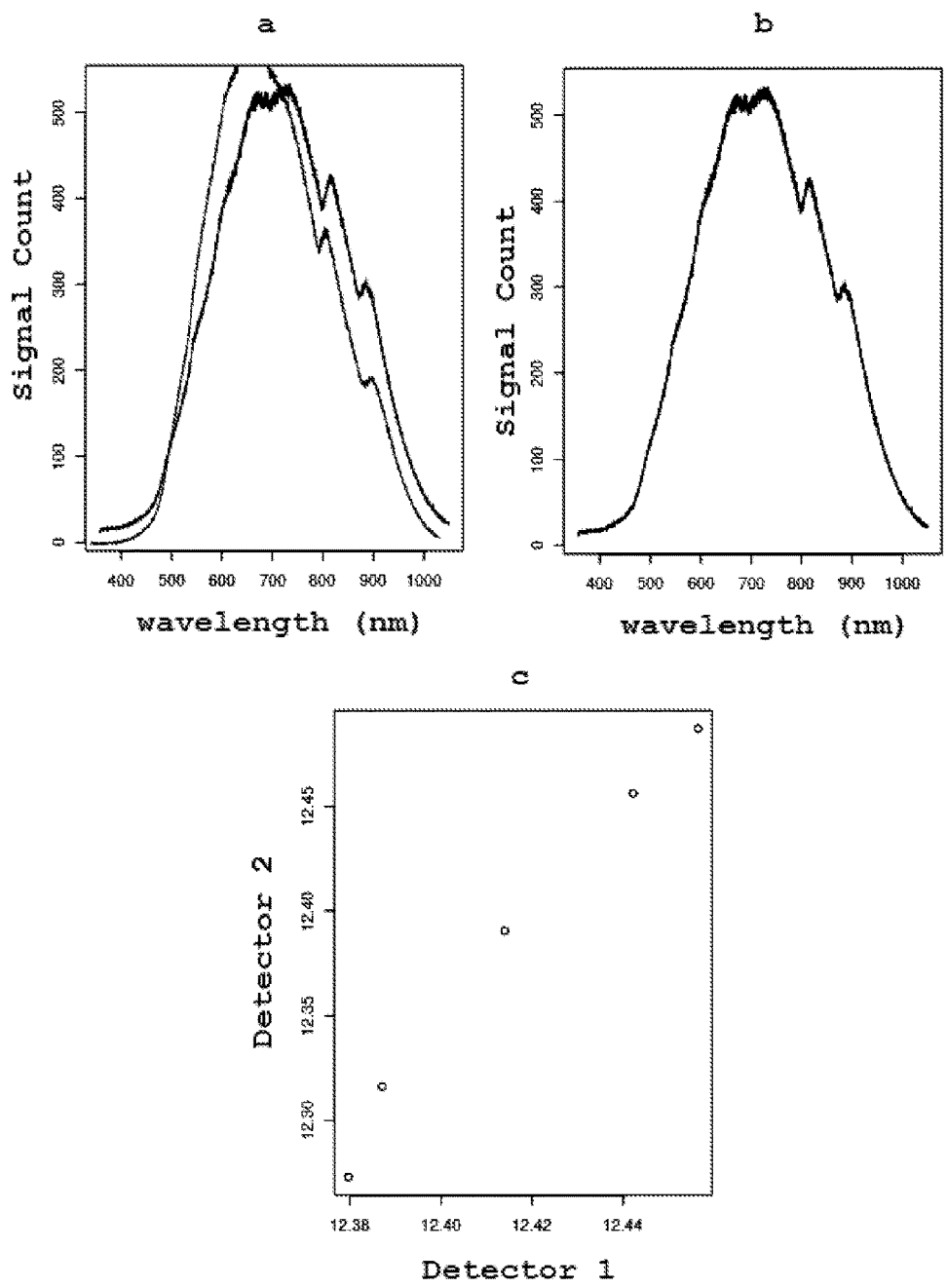
FIG. 5B spectral information transfer between detectors of 0.54 nm and 2.87 nm optical resolution with a halogen-tungsten light source.

FIG. 5A shows how spectral information transfer between detectors of 0.54 nm and 2.87 nm optical resolution with a mercury reference light source; and FIG. 5B illustrates spectral information conversion between detectors of 0.54 nm and 2.87 nm optical resolution with a halogen-tungsten light source, without the need of calibration transfer.

Spectral conversion is performed using the following procedure. After the spectra is recorded, the following spectral information transfer method (FIG. 4A (a)) is used:

Stretch the reference recorded spectra to a higher pixel resolution (preferably always greater than three times, using interpolation for the missing data);

Perform super-resolution to obtain higher spectral full width at half maximum (FWHM) than the optical limit:
  use the spectral replicates to develop the interpolation model of the full pixel resolution by local regression;
  perform deconvolution to resolve convolved information below optical resolution;

Perform local peak warping and compute distances between the reference spectra and the recorded spectra, and repeat local warping until the correlation value between the recorded spectra and reference spectra is above the threshold, and if so, proceed;

Convert the spectra between spectrometer by a relational model, and store the relation ratios in a convertion matrix. This matrix can now be used to both stretch and convert directly any new spectrometer spectra into a universal detector.

Example (a)—Holistic monitoring of body fluids: Tables 2, 3 and 4 present the correlations (R2) and limit of detection (DL) between the spectral fingerprint and quantified metabolites of a large population study using the present system with: I) 10270 serum samples; ii) 2730 whole blood samples; iii) 3480 urine samples; smaller samples for iv) pulse veins and v) fat tissue biopsies. As a realization example, we provide the following analytical quantifications for: i) blood serum (table 2): glucose (mg/dl), urea (mg/dl), creatinine (mg/dl), alanine aminotransferase (ALT) (UP), aspartate aminotransferase (AST) (UP), cholesterol (mg/dl), triglycerides (mg/dl), uric acid (mg/dl), alkaline phosphatase (ALP) (UI/l), K (mmol/l), Na (mmol/l);

ii) whole blood (table 3): glucose (mg/dl), urea (mg/dl), creatinine (mg/dl), ALT (UI/l), AST (UI/l) cholesterol (mg/dl), triglycerides (mg/dl), uric acid (mg/dl), ALP (UI/l), K (mmol/l), Na (mmol/l), hemoglobin (g/dl), erythrocytes ($\times 10^{12}$/L), mean corpuscular volume (MCV) (fl), leukocytes ($\times 10^9$/L), platelets ($\times 10^9$/L); iii) urine: glucose (mg/dl), urea (mg/dl), creatinine (mg/dl), K (mmol/l), Na (mmol/l), Cl (mmol/l), Ca (mg/l), amylase (UI/l), total protein (mg/dl), micro-albumin (mg/dl), uric acid (mg/l);

iii) urine (table 4): glucose (mg/dl), urea (mg/dl), creatinine (mg/dl), K (mmol/l), Na (mmol/l), Cl (mmol/l), Ca (mg/l), amilase (ui/l), total protein (mg/dl), micro-albumin (mg/dl), uric acid (mg/l).

Example (b)—Probabilistic findings of diagnostic relevance of clinical states by means of a parameter of relevance to correlation of disease with spectral fingerprinting: Table 5 presents the correlation between diseases and the spectral fingerprinting parameter, such as: i) diabetes mellitus, ii) renal insufficiency; iii) hyperuricemia; iv) hepatic insufficiency; iv) inflammation; and v) dyslipidemia. The probabilistic models were obtained opposing the spectra collected in the blood serum and against the clinical data analyzed by a panel of medical experts. The discriminatory capacity between the group of patients/healthy subjects is high, and these examples provide correct classification in 90% to 100%. The clinician will complement the metabolic information provided with other information and symptoms, to have complete information in real time and to be able decide diagnosis on time at the point of care. For example, a patient presenting rating close to 100% for diabetes mellitus (as a result of high levels of glucose) should then be medically evaluated to initiate the appropriate therapeutic plan, which can range from dietary advice to prescription therapy with oral anti-diabetic agents or insulin.

Example (c)—Use in clinic algorithms for point-of-care findings of diagnostic relevance: presents the possibility for quantification of troponin I and myoglobin; these biomarkers are critical in helping to establish the possibility of an acute ischemic heart syndrome in real-time. Furthermore, it can be also use to quantify proteins/enzymes, e.g. PSA, which are of interest as tumor markers.

Example (d)—High-throughput, large scale population findings of diagnostic relevance and epidemiologic characterization: Table 6 shows the predicted characterization of our spectral database using the probabilistic models, which allow the fast characterization of large populations at the point-of-care (by non-invasive reflectance probe emission and reflectance of spectra from the subjects' body, in this case blood vessels, simulated and real).

Non-invasive determination of: glucose (mg/dl), urea (mg/dl), creatinine (mg/dl), cholesterol (mg/dl), cholesterol HDL (mg/dl), triglycerides (mg/dl), ALT (ui/l), AST (ui/l), Albumin (mg/dl), hemoglobin (g/dl), erythrocytes, MCV, leukocytes, platelets, hematocrit, mean corpuscular hemoglobin, neutrophiles, eosinophiles, lymphocytes and ALP (ui/l).

Example (e)—non-invasive reflectance probe emission and reflectance of spectra from the subjects' body: in this case adipose tissue, an example not involving a blood vessel or blood sample, thus obtaining through reflectance from fat (adipose) tissue: triglycerides (mg/l).

TABLE 1

Optical properties of different detectors

| | Pixel Number | Pixel Size (micron) | Range (nm) | Slit (micron) | Resolution (nm) |
|---|---|---|---|---|---|
| 1 | 1024 | 7.8 | 200-1200 | 5 | 1.99 |
| 2 | 1024 | 7.8 | 200-1200 | 10 | 3.57 |
| 3 | 1024 | 7.8 | 200-1200 | 25 | 5.93 |
| 4 | 1024 | 7.8 | 200-1200 | 50 | 11.87 |
| 5 | 1024 | 7.8 | 200-1200 | 100 | 23.75 |
| 6 | 2048 | 14 | 200-1200 | 5 | 0.57 |
| 7 | 2048 | 14 | 200-1200 | 10 | 1.1 |
| 8 | 2048 | 14 | 200-1200 | 25 | 2.87 |
| 9 | 2048 | 14 | 200-1200 | 50 | 4.54 |
| 10 | 2048 | 14 | 200-1200 | 100 | 9.0 |
| 11 | 3648 | 8 | 200-1200 | 5 | 0.54 |
| 12 | 3648 | 8 | 200-1200 | 10 | 0.92 |
| 13 | 3648 | 8 | 200-1200 | 25 | 1.65 |
| 14 | 1024 | 284 | 200-1200 | 5 | 0.21 |
| 15 | 1024 | 284 | 200-1200 | 10 | 0.53 |
| 16 | 1024 | 284 | 200-1200 | 25 | 0.98 |
| 17 | 1024 | 284 | 200-1200 | 50 | 1.19 |
| 18 | 1024 | 284 | 200-1200 | 100 | 2.38 |

TABLE 2

Blood serum metabolite quantification and correlation with spectral fingerprinting

| | Detector 1 | | | | | | Detector 2 | | Detector 3 | | Detector 4 | |
|---|---|---|---|---|---|---|---|---|---|---|---|---|
| | Uv-Vis* | | Vis-Nir** | | Vis-Nir*** | | Vis-Nir*** | | Vis-Nir*** | | Raman | |
| Metabolite | R2 | DL | R2 | DL | R2 | DL | R2 | DL | R2 | DL | R2 | DL |
| Glucose (mg/dl) | 0.95 | 10.3 | 0.97 | 8.6 | 0.97 | 7.6 | 0.98 | 5.74 | 0.98 | 2.6 | 0.98 | 8.2 |
| Urea (mg/dl) | 0.99 | 4.2 | 0.98 | 5.7 | 0.98 | 3.1 | 0.98 | 2.93 | 0.99 | 30.2 | 0.95 | 5.1 |
| Creatinine (mg/dl) | 0.98 | 0.08 | 0.98 | 0.06 | 0.97 | 0.05 | 0.95 | 7.2 | 0.98 | 0.08 | 0.98 | 0.05 |
| ALT (ui/l) | 0.99 | 5.9 | 0.97 | 7.8 | 0.98 | 6.4 | 0.98 | 5.63 | 0.99 | 5.9 | 0.99 | 7.2 |
| AST (ui/l) | 0.98 | 6.4 | 0.99 | 2.2 | 0.98 | 3.1 | 0.99 | 2.36 | 0.98 | 6.4 | 0.97 | 2.5 |
| Cholesterol (mg/dl) | 0.93 | 21.1 | 0.97 | 11.3 | 0.96 | 13.1 | 0.98 | 7.46 | 0.93 | 21.2 | 0.99 | 11.8 |
| Triglycerides (mgl/dl) | 0.99 | 6.8 | 0.99 | 12.7 | 0.98 | 7.8 | 0.98 | 6.98 | 0.99 | 6.8 | 0.99 | 11.9 |
| Uric Acid (mg/dl) | 0.98 | 0.5 | 0.97 | 0.6 | 0.98 | 0.3 | 0.95 | 0.19 | 0.98 | 0.5 | 0.98 | 0.8 |
| ALP (ui/l) | 0.99 | 12.3 | 0.97 | 12.9 | 0.99 | 3.4 | 0.98 | 28.3 | 0.99 | 12.4 | 0.95 | 11.7 |
| K (mmol/l) | 0.99 | 0.2 | 0.98 | 0.09 | 0.97 | 0.08 | 0.97 | 0.08 | 0.99 | 0.2 | 0.95 | 0.09 |
| Na (mmol/l) | 0.95 | 1.2 | 0.95 | 1.0 | 0.85 | 1.0 | 0.93 | 0.93 | 0.95 | 1.2 | 0.75 | 3.3 |
| Myoglobin (ug/l) | 0.89 | 44.9 | 0.98 | 14.4 | | | | | | | | |
| Troponin I (ug/l) | 0.84 | 0.12 | 0.95 | 0.20 | | | | | | | | |

*200-320 nm;
**320-1200 nm;
***350-850 nm

TABLE 3

Blood metabolite quantification and correlation with spectral fingerprinting

| Metabolite | Detector 2 Vis-Nir* | | Detector 3 Vis-Nir* | | Detector 4 Raman | |
|---|---|---|---|---|---|---|
| | R2 | DL | R2 | DL | R2 | DL |
| Glucose (mg/dl) | 0.99 | 4.0 | 0.92 | 12.1 | 0.98 | 4.18 |
| Urea (mg/dl) | 0.92 | 26.5 | 0.95 | 4.8 | 0.99 | 4.85 |
| Creatinine (mg/dl) | 0.99 | 0.08 | 0.95 | 0.3 | 0.99 | 0.09 |
| ALT (ui/l) | 0.97 | 0.17 | 0.95 | 2.5 | 0.98 | 1.9 |
| AST (ui/l) | 0.98 | 0.89 | 0.99 | 0.3 | 0.99 | 0.85 |
| Cholesterol (mg/dl) | 0.99 | 1.31 | 0.99 | 1.31 | 0.99 | 0.94 |
| Triglycerides (mg/dl) | 0.83 | 8.32 | 0.67 | 12.9 | 0.99 | 5.5 |
| Uric Acid (mg/dl) | 0.99 | 0.03 | 0.99 | 0.04 | 0.99 | 0.36 |
| ALP (ui/l) | 0.90 | 15.0 | 0.90 | 19.0 | 0.98 | 17.39 |
| K (mmol/l) | 0.99 | 0.08 | 0.97 | 0.1 | 0.97 | 0.08 |
| Na (mmol/l) | 0.98 | 1.7 | 0.92 | 1.6 | 0.98 | 1.25 |
| Hemoglobin (g/dl) | 0.97 | 0.68 | 0.93 | 0.8 | 0.95 | 0.33 |
| Erythrocytes ($\times 10^{12}$/L) | 0.95 | 0.15 | 0.92 | 0.3 | 0.98 | 0.56 |
| MCV (fL) | 0.98 | 0.05 | 0.98 | 0.07 | 0.99 | 2.8 |
| Leukocytes ($\times 10^9$/L) | 0.91 | 2.0 | 0.83 | 2.26 | 0.98 | 0.41 |
| Platelets ($\times 10^9$/L) | 0.92 | 35.2 | 0.90 | 39.22 | — | — |

*320-1200 nm

TABLE 4

Urine quantification and correlation with spectral fingerprinting

| Metabolite | Detector 1 Uv-Vis* | | Detector 1 Vis-Nir** | | Detector 2 Vis-Nir** | | Detector 3 Vis-Nir** | | Detector 4 Raman | |
|---|---|---|---|---|---|---|---|---|---|---|
| | R2 | DL | R2 | DL | R2 | DL | R2 | DL | R2 | DL |
| Glucose (mg/dl) | — | — | — | — | — | — | 0.98 | 2.6 | — | — |
| Urea (mg/dl) | 0.99 | 0.1 | 0.98 | 0.08 | 0.99 | 0.1 | 0.99 | 0.1 | 0.98 | 0.2 |
| Creatinine (mg/dl) | 0.98 | 3.5 | 0.97 | 6.4 | 0.98 | 2.9 | 0.99 | 0.63 | 0.99 | 3.2 |
| K (mmol/l) | 0.99 | 1.2 | 0.99 | 1.0 | 0.99 | 1.3 | 0.99 | 1.34 | 0.99 | 1.0 |
| Na (mmol/l) | 0.99 | 0.9 | 0.98 | 0.9 | 0.99 | 0.8 | 0.99 | 0.88 | 0.97 | 0.8 |
| Cl (mmol/l) | — | — | — | — | — | — | 0.95 | 12.0 | — | — |
| Ca (mg/l) | — | — | — | — | — | — | 0.99 | 0.33 | — | — |
| Amilase (ui/l) | — | — | — | — | — | — | 0.99 | 2.87 | — | — |
| Total Protein (mg/dl) | 0.99 | 7.2 | 0.99 | 5.2 | 0.99 | 5.2 | 0.95 | 0.81 | 0.99 | 8.5 |
| Micro-Albumin (mg/dl) | 0.97 | 24.03 | 0.97 | 4.13 | 0.97 | 4.13 | 0.99 | 2.02 | 0.99 | 4.8 |
| Uric Acid (mg/l) | 0.99 | 0.02 | 0.98 | 0.05 | 0.98 | 0.04 | 0.97 | 0.05 | — | — |

*200-320 nm;
**320-1200 nm

TABLE 5

Probabilistic parameter of relevance to disease correlation with spectral fingerprinting

| Probabilistic parameter of relevance to: | Serum Uv-Vis* | | Serum Vis-Nir** | | Blood Vis-Nir** | | Classification Ratio (%) |
|---|---|---|---|---|---|---|---|
| | R2 | LD | R2 | LD | R2 | LD | |
| Diabetes Mellitus | 0.96 | 0.14 | 0.85 | 0.27 | 0.89 | 0.18 | 100 |
| Renal insufficiency | 0.87 | 0.25 | 0.87 | 0.26 | 0.99 | 0.07 | 100 |
| Hyperuricemia | 0.99 | 0.03 | 0.99 | 0.05 | — | — | 100 |
| Hepatic insufficiency | 0.80 | 0.33 | 0.78 | 0.31 | 0.99 | 0.02 | 100 |
| Inflammation | 0.80 | 0.33 | 0.82 | 0.36 | 0.82 | 0.19 | 91 |
| Dyslipidemia | 0.83 | 0.36 | 0.91 | 0.29 | 0.94 | 0.30 | 100 |

*200-320 nm;
**320-1200 nm

TABLE 6

Non-invasive reflectance probe blood quantification and correlation with spectral fingerprinting of both tylose artificial vein model (vessels A-C) and voluntary subject measurements at their wrist veins; (200-1200 nm); skin depths are indicated.

| | Vessel A (6.5 mm) | Vessel B (3 mm) | Vessel C (1 mm) | Pulse Veins (1.5 to 1 mm) | |
|---|---|---|---|---|---|
| | R2 | R2 | R2 | R2 | DL |
| Glucose (mg/dl) | 0.75 | 0.95 | 0.97 | 0.91 | 4.78 |
| Urea (mg/dl) | 0.62 | 0.67 | 0.98 | 0.95 | 2.07 |
| Creatinine (mg/dl) | 0.98 | 0.99 | 0.83 | 0.97 | 0.03 |
| Cholesterol (mg/dl) | 0.87 | 0.99 | 0.99 | 0.96 | 6.86 |
| Cholesterol HDL (mg/dl) | — | — | — | 0.96 | 4.54 |
| Cholesterol LDL (mg/dl) | — | — | — | 0.97 | 4.45 |

TABLE 6-continued

Non-invasive reflectance probe blood quantification and correlation with spectral fingerprinting of both tylose artificial vein model (vessels A-C) and voluntary subject measurements at their wrist veins; (200-1200 nm); skin depths are indicated.

| | Vessel A (6.5 mm) | Vessel B (3 mm) | Vessel C (1 mm) | Pulse Veins (1.5 to 1 mm) | |
|---|---|---|---|---|---|
| | $R^2$ | $R^2$ | $R^2$ | $R^2$ | DL |
| Triglycerides (mg/dl) | 0.80 | 0.99 | 0.87 | 0.93 | 18.39 |
| ALT (ui/l) | 0.93 | 0.98 | 0.95 | 0.96 | 1.86 |
| AST (ui/l) | — | — | — | 0.96 | 2.76 |
| Albumin (mg/dl) | — | — | — | 0.98 | 0.09 |
| Hemoglobin (g/dl) | 0.97 | 0.85 | 0.85 | 0.98 | 0.26 |
| Erythrocytes | 0.93 | 0.88 | 0.99 | 0.98 | 0.11 |
| MCV f(l) | 0.97 | 0.96 | 0.98 | 0.96 | 0.94 |
| Leukocytes | 0.98 | 0.75 | 0.91 | 0.97 | 0.37 |
| Platelets | — | — | — | 0.94 | 12.92 |
| Hematocrit | — | — | — | 0.98 | 0.74 |
| Mean Corpuscular Hemoglobin | — | — | — | 0.97 | 0.37 |
| Neutrophils | — | — | — | 0.94 | 3.28 |
| Eosinophils | — | — | — | 0.98 | 0.25 |
| Lymphocytes | — | — | — | 0.94 | 3.08 |
| ALP (U/l) | 0.98 | — | 0.98 | 0.97 | 4.62 |

TABLE 7

Adipose tissue metabolite quantification and correlation with spectral analysis

| | Vis-Nir* | |
|---|---|---|
| | $R^2$ | DL |
| Triglycerides (mg/l) | 0.94 | 534 |

*320-1200 nm

In an aspect of the disclosure, the body fluid or tissue to be characterized is of an animal, in particular a warm-blooded animal or a mammal. In another aspect of the disclosure, the body fluid or tissue to be characterized is of a domesticated animal. In yet another aspect of the invention, the body fluid or tissue to be characterized is of a fish, in particular farmed fish.

Examples of domesticated animals are cattle, dog, cat, swine, horse, pony, donkey, sheep, goat, cow, bull, rabbit, chicken, duck, turkey and ostrich, among others. Examples of mammals are dog, cat, swine, horse, pony, donkey, sheep, goat, rabbit, deer, bison, buffalo, zebra, bear, wolf, monkey species, otter, sea lion, seal, dolphin, lion, tiger, leopard, kangaroo, elephant, and hippopotamus, among others. Examples of fish, in particular farmed fish, are barramundi, bass species, bream species, carp species, cod species, perch, salmon, tuna, trout, and tilapia, among others.

The above described embodiments are combinable. In the tables, values not shown were not obtained or are not applicable.

The following claims set out particular embodiments of the disclosure.

Citations of Patent Literature

U.S. Pat. No. 6,167,290, U.S. Pat. No. 7,330,746B2, U.S. Pat. No. 8,013,991B2, U.S. Pat. No. 7,330,746, U.S. Pat. No. 566,956, U.S. Pat. No. 4,890,619, EP1620002B1, U.S. Pat. No. 6,167,290, U.S. Pat. No. 6,064,897, GB2489717A, U.S. Pat. No. 7,524,671B2, U.S. Pat. No. 7,688,440B2.

Citations of Non-Patent Literature

Burns D A, Ciurczak E W. 2001. Handbook of near-infrared analysis. 2nd Ed. Marcell Dekker, Inc., NY.
In the Field of Analytical Chemistry:
[10] Talke, H, Schubert, G E 1965 Enzyme determination of urea in blood serum by the Warburg optical test. Klinische Wochenschrift 43 174-175
[11] Jaffe M. Ueber den Niederschlag, welchen Pikrinsaure in normalem Harn erzeugt und uber eine neue Reaction des Kreatinins. Hoppe Seylers Z Physiol Chem 1886; 10:391-400.
[12] Richmond W. Preparation and properties of a cholesterol oxidase from *Nocardia* sp. and its application to the enzymatic assay of total cholesterol in serum. Clin Chem 1973; 19(12):1350-6.
[13] Allain C C, Poon L S, Chan C S, et al. Enzymatic determination of total serum cholesterol. Clin Chem 1974; 20(4):470-5.
[14] Fossati P, Prencipe L. Serum triglycerides determined colorimetrically with an enzyme that produces hydrogen peroxide. Clin Chem 1982; 28:2077-80.
[15] McGowan M W, Artiss J D, Strandbergh D R, et al. A peroxidase-coupled method for the colorimetric determination of serum triglycerides. Clin Chem 1983; 29:538-42
[16] Trivedi R, Rebar L, Berta E, et al. New enzymatic method for serum uric acid at 500 nm. Clin Chem 1978; 24(11):1908-11.
[17] Kabasakalian P, Kalliney S, Wescott A. Determination of uric acid in serum, with use of uricase and tribromophenol-aminoantipyrine chromogen. Clin Chem 1973; 19:522
[18] Tietz N W, Burtis C A, Duncan P, et al. A reference method for measurement of alkaline phosphatase activity in human serum. Clin Chem 1983; 29(5):751-6
In the Field of Calibration Transfer:
Burns D A, Ciurczak E W. 2001. Handbook of near-infrared analysis. 2nd Ed. Marcell Dekker, Inc., NY.
Feudale R N, Woody N A, Tan H, Myles A J, Brown S D, Ferre J. 2002. Transfer of multivariate calibration models: a review. Chemo. Intl. Lab. Sys. 64: 181-192.
Woody N A, Feudale R N, Myles A J, Brown S D. 2004. Transfer of multivariate calibration between four near infrared spectrometers using orthogonal signal correction. Anal Chem. 2004 May 1; 76(9):2595-600.
Wangdong Ni, Steven D Brown, Ruilin Man. 2011. Stacked PLS for calibration transfer without standards. J. Chemometrics, 25: 130-137
Forina M. et al. 1995. Transfer of calibration function in near infrared spectroscopy. Chem. and Int. Lab. Sys. 27(2): 189-203.
Fan W, Liang Y, Yuan D, Wang J. 2008. Calibration model transfer for near-infrared spectra based on canonical correlation analysis. Analytica Chimica Acta, 623(1): 22-29
Andrews D T, Warzel P P. 1997. Application of maximum likelihood principal component analysis: incomplete datasets and calibration transfer. Analytical Chemica Acta, 350: 341-352.
Xie Y, Hopke P K 1999. Calibration transfer as a data reconstruction problem. Analytical Chemica Acta, 384: 193-205.
Despagne F, Massart D L, Jansen M, Daalen H. 2000. Intersite transfer of industrial calibration models. Analytical Chemica Acta, 384: 193-205.
Ni W, Brown S D, Man R. 2010. Data fusion in multivariate calibration transfer. Analytical Chemica Acta, 661: 133-142.

Shenk J S, Westerhaus M O. U.S. Pat. No. 4,866,644. Sep. 12, 1991.

Shenk J S, Westerhaus M O. 1996. New standardization and calibration procedures for NIRS analytical systems. Crop Science, 31:1694-1696.

Wang Y, Kowalski B R. 1992. Calibration transfer and measurement stability of NIR spectrometers. Applied Spectroscopy, 46: 764-771.

Wang Y, Veltkamp D J, Kowalski B R. 1991 Multivariate instrument standardization. Anal. Chem. 63(23): 2750-2756

Barring H K, Boelens H F M, Noord O E, Smilde, A K. 2001. Optimizing meta-parameters in continuous piecewise direct standardization. Applied Spectroscopy, 55(4): 458-466

Geladi P, Barring H, Dabakk E, Trygg J, Antti H, Wold S, Karlberg B. 1999. Calibration transfer for predicting lake-water pH from near infrared spectra of lake sediments. Journal of Near Infrared Spectroscopy, 7:251-264

Walzack B, Massart D L. 1997. Wavelet packet transform applied to a set of signals: a new approach to the best basis selection. Chem. Intel. Lab Sys. 78: 39-50.

Walzack B, Bouveresse E, Massart D L. 1997. Standardization of near infrared spectra in the wavelet domain. Chem. Intel. Lab Sys. 36: 41-51.

Lerner J M. 2006. Imaging spectrometer fundamentals for resarchers in the biosciences—a tutorial. Cytometry Part A 69A: 712-734.

Kauppinen J., Partanen J. 2001. Fourier transforms in spectroscopy. Wiley-VCH, Berlin.

The invention claimed is:

1. An optical system for parameter characterization of an element of body fluid or tissue comprising an optical device which comprises:
   a light source for emitting light onto the element;
   a chamber for holding an element of body fluid or tissue, wherein the chamber includes a reference sample;
   a sample spectrometer for recording the spectrum of light from the element of body fluid or tissue, said light from the element being of transmittance, reflectance or Raman scattering of the emitted light by said element and the spectrum of light from the reference sample;
   the optical system further comprising a processor having a memory and configured
   to compare the recorded spectrum of the reference sample to a stored value within the memory, by obtaining a higher spectral full width at half maximum (FWHM) than that of an optical limit of the spectrometer by:
   (1) calculating an interpolation model of the higher pixel resolution by local regression, and interpolating the obtained reference spectral measurements;
   (2) performing deconvolution of the interpolated spectral measurements by an apodization function of the optical device to resolve convolved information below optical resolution; and
   (3) comparing the convoluted spectral measurements to a stored reference spectral measurement of the reference sample,
   where the convoluted spectral measurement of the reference sample is substantially similar to the stored reference measurement, convert the recorded spectrum of the element of body fluid or tissue using a conversion matrix into a standardized spectrum, wherein said conversion matrix has been obtained by calibrating the optical system spectrum response against a spectrum reference previously measured by a reference spectrometer;
   pre-process the converted spectrum by correcting the standardized spectrum for at least scattering;
   correlate, for parameter quantification, the converted pre-processed spectrum with pre-obtained spectral bands for each parameter previously measured by the reference spectrometer; wherein said the recorded spectrum is within the ultraviolet—visible—near infrared wavelengths.

2. An optical system according to claim 1 wherein the spectral bands for each parameter were pre-obtained by:
   obtaining sample spectra with the reference spectrometer for known parameter values;
   pre-processing the obtained sample spectra;
   correlating the pre-processed spectra with the known parameter values in order to obtain the spectral bands for each parameter.

3. An optical system according to claim 2 wherein the spectral bands for each parameter were pre-obtained, explicitly or implicitly, by correlation through multivariate regression, latent variable model, partial least squares, two-step partial least squares, sparse partial least squares, canonical correlation, artificial neural network or support vector machines.

4. An optical system according to claim 1 wherein the spectrum calibrating for obtaining said conversion matrix comprises computing the warping of a conversion matrix function to match both the frequency and intensity of the spectra of the optical device spectrum response against the frequency and intensity of the spectrum reference previously measured by the reference spectrometer.

5. An optical system according to claim 4 wherein the spectrum calibrating for obtaining said conversion matrix comprises:
   recording a spectrum of a spectrum reference of the same light emitting, reflecting, absorbing or scattering material of the previously recorded spectrum reference by the reference spectrometer;
   pre-processing the recorded spectrum;
   computing the warping of said conversion matrix function such that the pre-processed recorded spectrum converted by said matrix matches the frequency and intensity of the previously recorded spectrum reference.

6. An optical system according to claim 5 wherein pre-processing of a spectrum further comprises correcting the spectrum for Mie and Rayleigh scattering, and correcting for baseline-stray light.

7. An optical system according to claim 1 wherein the processor is configured to operate the spectrometer when recording a spectrum in piecewise measurement in a plurality of overlapping intervals covering the wavelength range to be recorded of the spectrometer, each interval optimized in both integration time and light intensity for being substantially within the optimum sensitivity and linear region of the spectrometer.

8. An optical system according to claim 1 wherein the processor is configured such that the spectrum recording comprises interpolation of the received spectra to a resolution at least three (3) times higher than the original spectra.

9. An optical system according to claim 1 wherein processor is configured such that spectrum recording comprises the steps of:
   recording a sample spectrum without the element of body fluid or tissue to be characterized; and
   linearly calibrating the spectrometer for each frequency such that the sample spectrum matches a previously obtained reference spectrum.

10. The optical system according to claim 9 wherein the element of body fluid or tissue to be characterized is a sample of a body fluid.

11. An optical system according to claim 10 wherein the chamber comprises one or more mirrors for reflecting the light from the light source through the element of body fluid or tissue to be characterized to the spectrometer, wherein at least one of the mirror or mirrors is attached to the chamber lid.

12. The optical system according to claim 11 comprising one mirror in the chamber, said mirror being arranged distal to the optical device to reflect light back to the optical device, and comprising one mirror coupled to the optical device said mirror being arranged to reflect light back to the element of body fluid or tissue to be characterized.

13. An optical system according to claim 1 wherein the chamber has a lid for receiving the sample.

14. An optical system according to claim 13 wherein the chamber is attachable to the optical device for characterization of the element of body fluid or tissue by magnets, mechanical pressure or mechanical fasteners.

15. An optical system according to claim 1 wherein the element of body fluid or tissue to be characterized is a body in-vivo element, and the optical system is arranged for parameter characterization of the body element by skin contact of the optical device, to a blood vessel or to adipose tissue body element.

16. An Optical system according to claim 1 comprising a plurality of light sources for emitting light onto the element of body fluid or tissue, a plurality of spectrometer inputs for recording the spectrum of light, and the processor is configured to select for the spectrometer, among the plurality of spectrometer inputs, the input or inputs which maximize the parameter quantification correlation with the pre-obtained spectral bands.

17. An optical system according to claim 16 wherein the optical device is a bracelet.

18. An optical system according to claim 1 wherein the parameter is one or more of the following: in urine, saliva, whole blood or blood serum sample, or in non-invasive in-vivo skin-contact to blood vessel or adipose tissue: glucose, urea, creatinine, ALT, AST, cholesterol, triglycerides, uric acid, ALP, K, Na, Cl, Ca, amylase, total protein, micro-albumin, hemoglobin, erythrocytes, mean corpuscular volume, leukocytes, platelets, troponin, and/or myoglobin.

19. An optical system according to claim 1 wherein the parameter is one or more of the following: probabilistic findings of intermediate diagnostic relevance of diabetes mellitus, renal insufficiency; hyperuricemia; hepatic insufficiency; inflammation; and/or dyslipidemia.

20. An optical system according to claim 1 wherein said recorded spectrum, is contained in the 200-2500 nm wavelengths.

* * * * *